(12) United States Patent
Chiou et al.

(10) Patent No.: US 8,846,633 B2
(45) Date of Patent: *Sep. 30, 2014

(54) METHOD FOR INHIBITING CANCER STEM CELL LIKE PROPERTIES AND CHEMORADIORESISTANT PROPERTIES OF CANCER OR TUMOR CELLS WITH MICRORNA145

(71) Applicant: Taipei Veterans General Hospital, Taipei (TW)

(72) Inventors: Shih-Hwa Chiou, Taipei (TW); Han-Shui Hsu, Taipei (TW); Jong-Yuh Cherng, Chiayi County (TW)

(73) Assignee: Taipei Veterans General Hospital, Taipei (TW)

( * ) Notice: Subject to any disclaimer, the term of this patent is extended or adjusted under 35 U.S.C. 154(b) by 0 days.

This patent is subject to a terminal disclaimer.

(21) Appl. No.: 13/671,274

(22) Filed: Nov. 7, 2012

(65) Prior Publication Data

US 2013/0115299 A1    May 9, 2013

Related U.S. Application Data

(60) Provisional application No. 61/556,642, filed on Nov. 7, 2011.

(51) Int. Cl.
| | | |
|---|---|---|
| *C12N 15/11* | (2006.01) | |
| *A61K 31/7088* | (2006.01) | |
| *C07H 21/02* | (2006.01) | |
| *A61K 31/7105* | (2006.01) | |
| *C12N 5/09* | (2010.01) | |
| *A61K 47/34* | (2006.01) | |
| *A61K 31/495* | (2006.01) | |
| *A61K 9/50* | (2006.01) | |
| *C12N 5/095* | (2010.01) | |

(52) U.S. Cl.
CPC ............ *A61K 31/7088* (2013.01); *C07H 21/02* (2013.01); *A61K 31/7105* (2013.01); *C12N 2501/65* (2013.01); *C12N 5/0693* (2013.01); *A61K 47/34* (2013.01); *A61K 31/495* (2013.01); *A61K 9/5031* (2013.01); *C12N 5/0695* (2013.01)
USPC ...................................................... 514/44 A

(58) Field of Classification Search
USPC ....................................................... 514/44 A
See application file for complete search history.

(56) References Cited

U.S. PATENT DOCUMENTS

| | | | | |
|---|---|---|---|---|
| 2008/0319039 | A1* | 12/2008 | Bersch et al. | 514/393 |
| 2009/0131356 | A1* | 5/2009 | Bader et al. | 514/44 |
| 2010/0047559 | A1* | 2/2010 | Nguyen et al. | 428/327 |
| 2010/0069471 | A1 | 3/2010 | Manoharan et al. | |
| 2012/0255043 | A1* | 10/2012 | Chiou et al. | 800/9 |
| 2013/0052238 | A1* | 2/2013 | Chiou et al. | 424/400 |
| 2013/0108691 | A1* | 5/2013 | Chiou et al. | 424/450 |

OTHER PUBLICATIONS

Cherng Curr. Pharm Biotechnol. 2011, 12:839-46.*
Koo et al. Molecular Biology of the Cell, Dec. 2010, vol. 21, abstract No. 3112/L087. Annual Meeting of the American Society for Cell Biology, pp. 1-3.*
Matthew Keith Ronck, The Role of miR-143 and miR-145 in the Invasion of Gliobastoma, A senior Scholar Thesis, 2010, pp. 1-25.
Hung et al., The synthesis of cationic polyurethanes to study the effect of amines and structures on their DNA transfection potential, Journal of Controlled Release, 2009, 133: 68-76.
Hsiao et al., Preparation of NSC Project Reports, 2007, pp. 1-6.

* cited by examiner

*Primary Examiner* — Brian Whiteman
(74) *Attorney, Agent, or Firm* — WPAT, P.C.; Anthony King

(57) ABSTRACT

The present invention provides a method for inhibiting cancer stem cell like properties and chemoradioresistant properties of cancer or tumor cells comprising delivering miR145 to the cancer or tumor cells, particularly brain tumor and head and neck cancer cells. The invention further provides a pharmaceutical composition comprising miR145 and a method for treating brain tumor and/or head and neck cancer comprising administration of miR145 to a subject in need thereof.

16 Claims, 17 Drawing Sheets

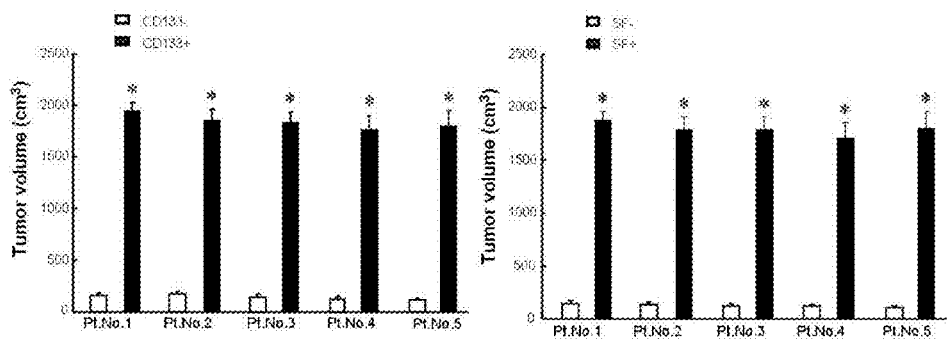
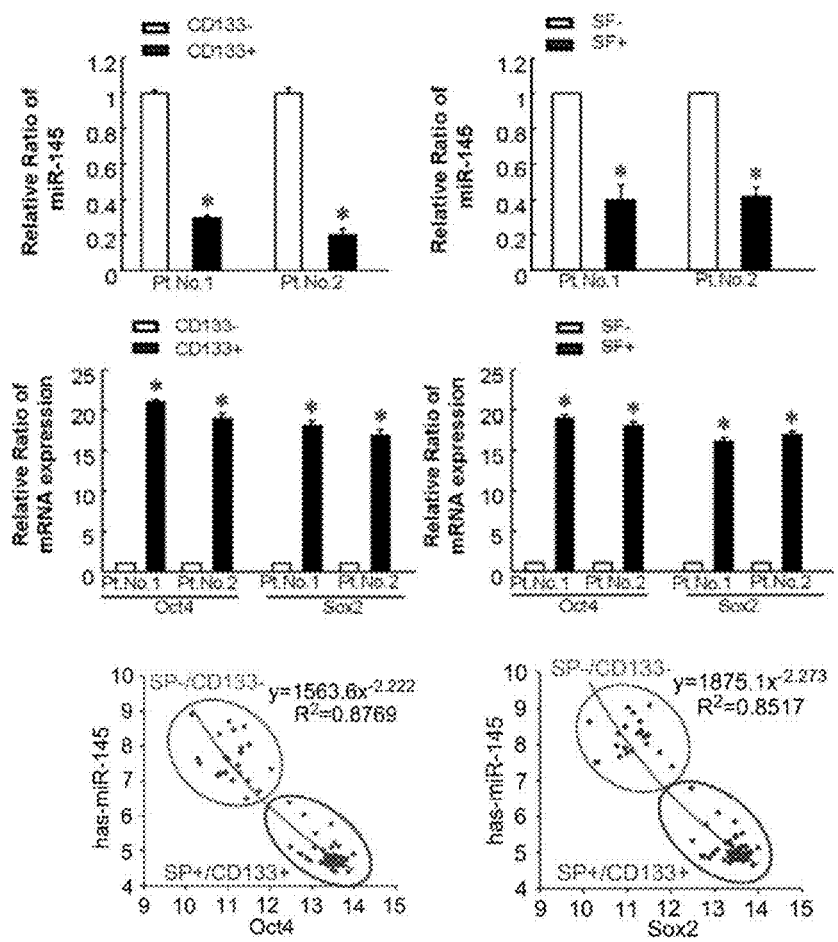
Figure 1-cont.

Figure 4-cont.

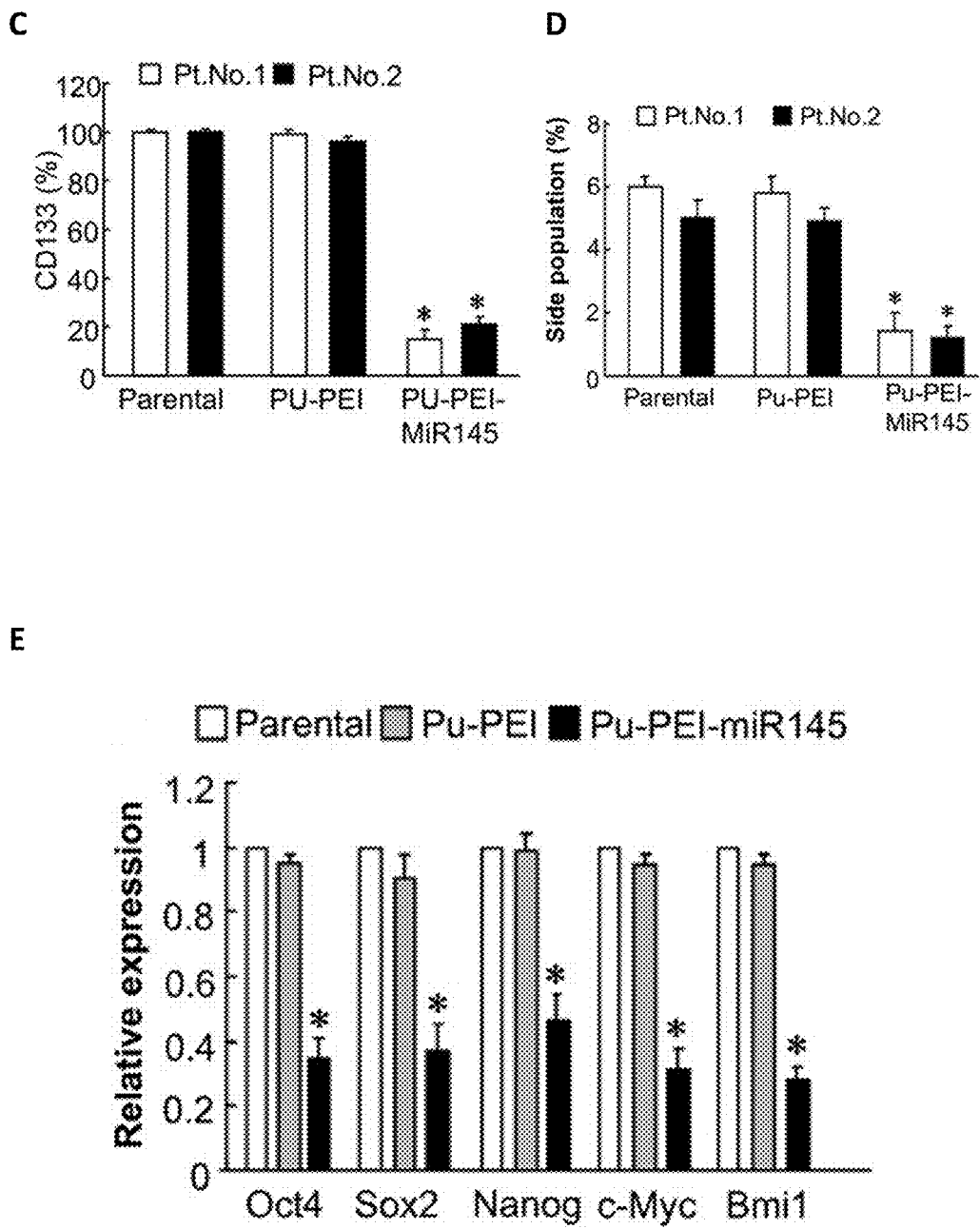
Figure 5-cont.

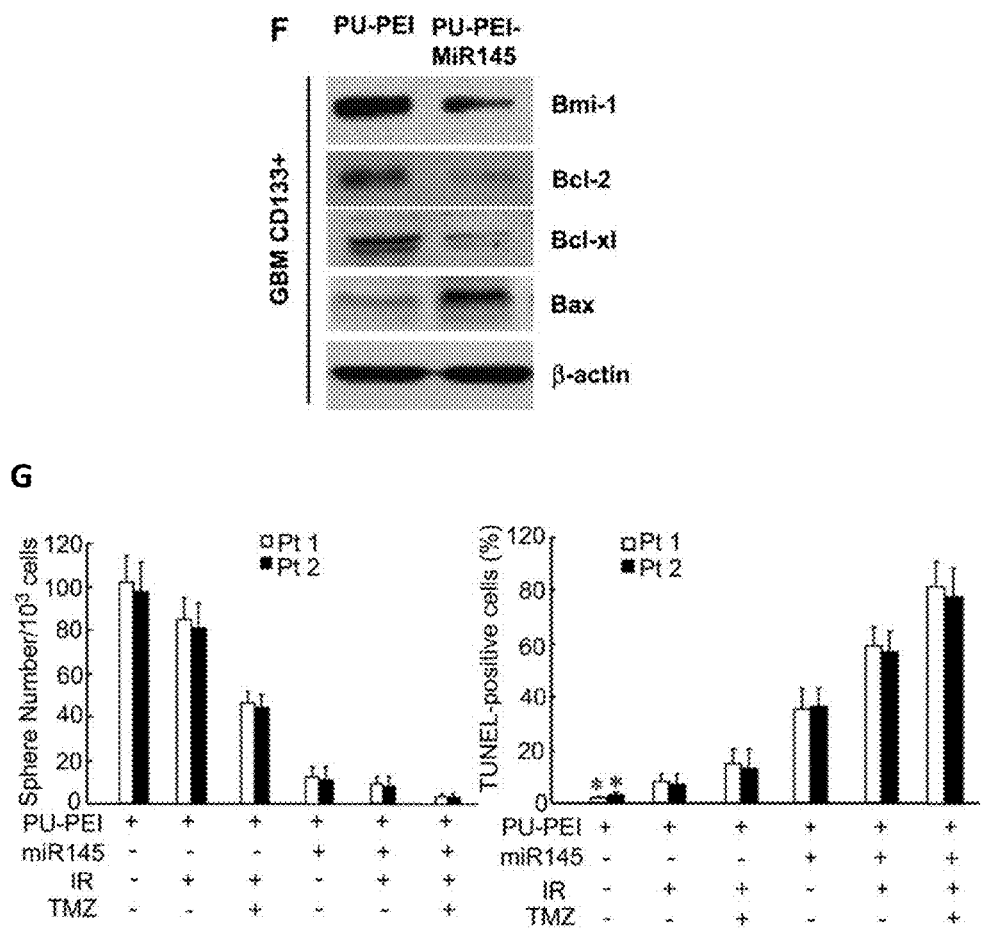
Figure 6-cont.

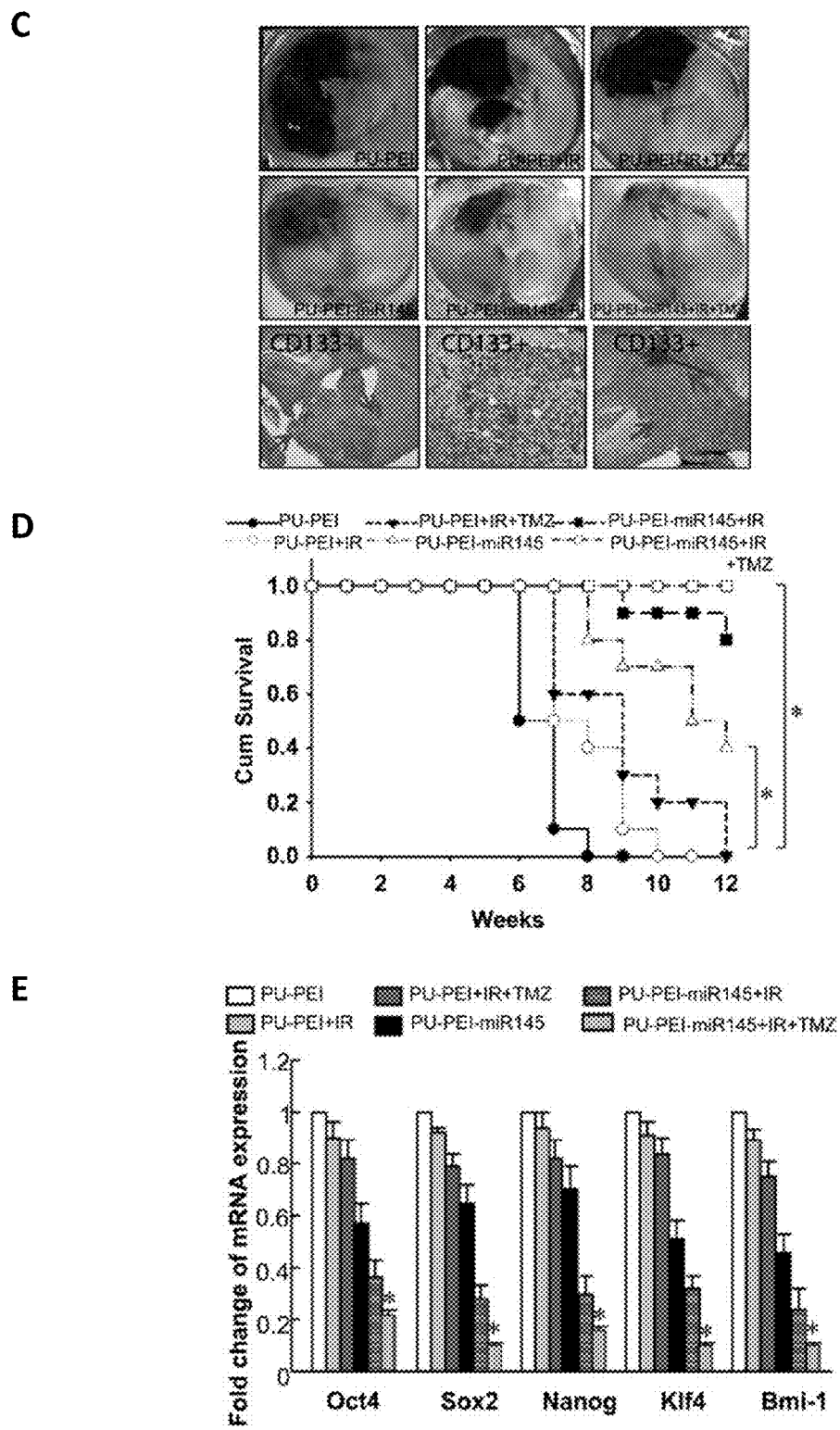
Figure 7-cont.

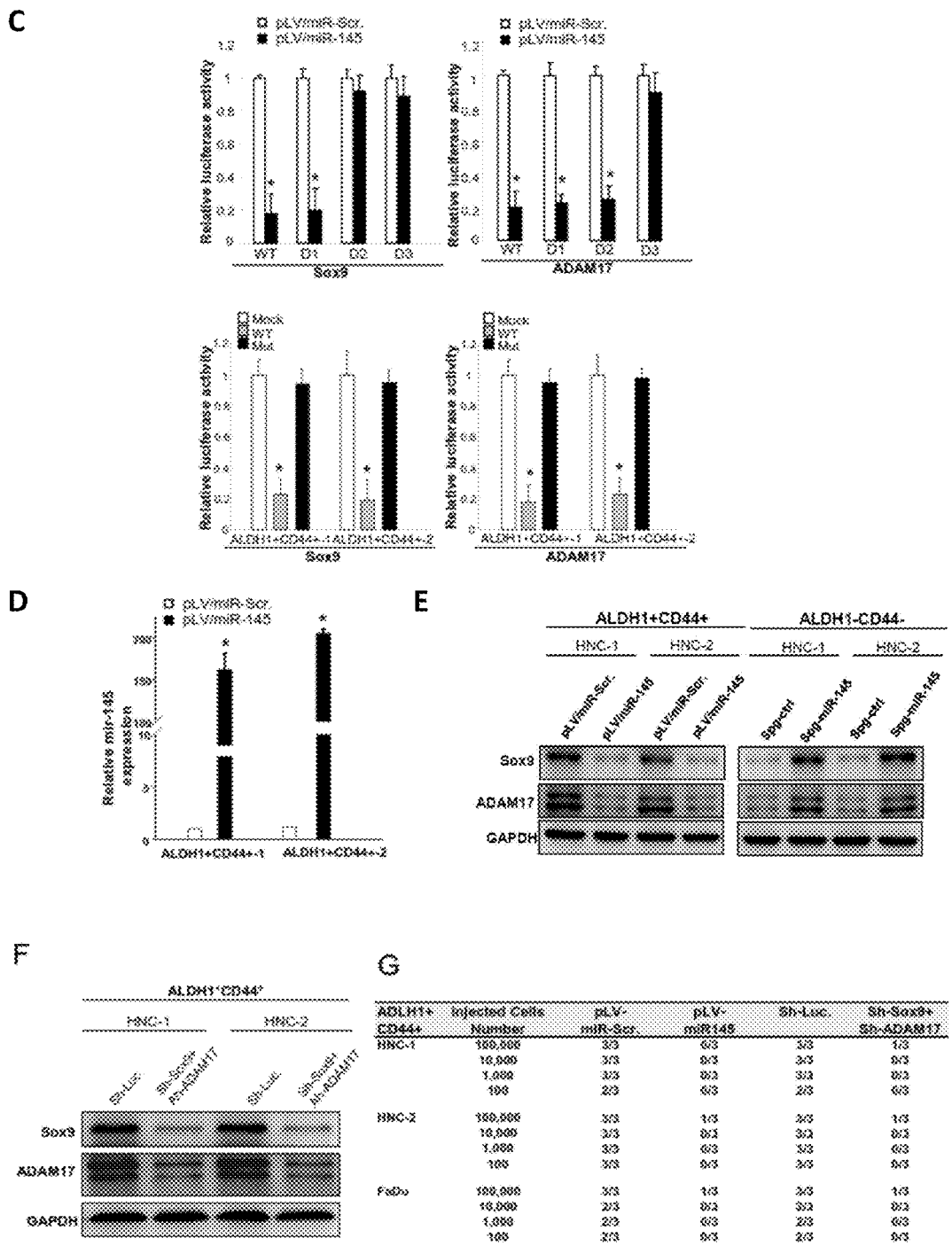
Figure 9-cont.

A

B

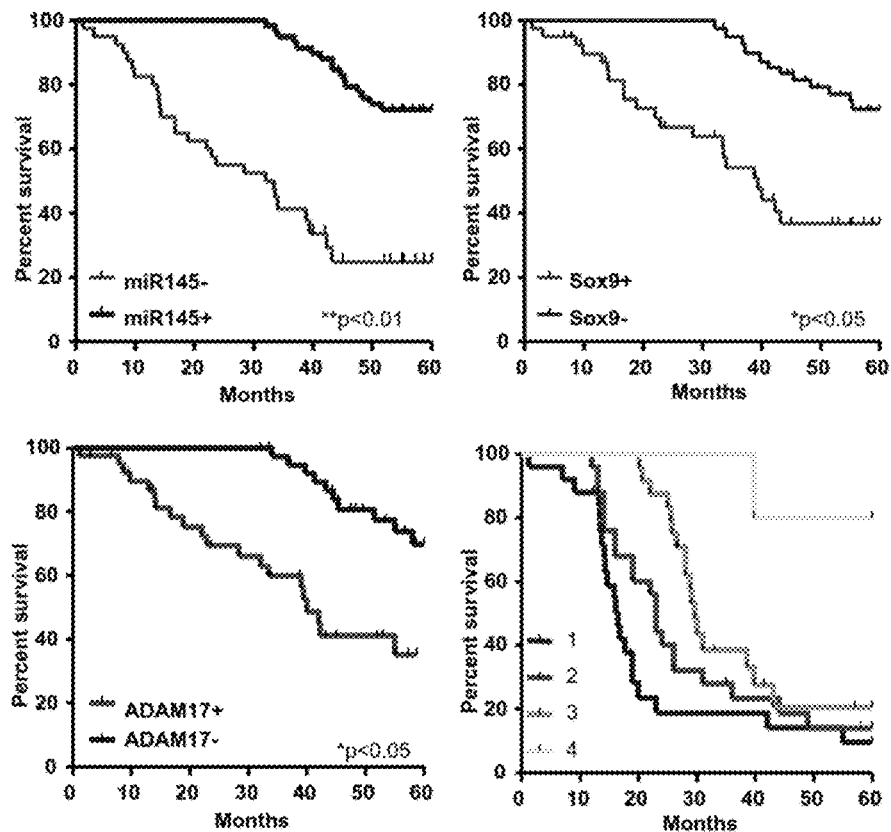
Figure 11-cont.

METHOD FOR INHIBITING CANCER STEM CELL LIKE PROPERTIES AND CHEMORADIORESISTANT PROPERTIES OF CANCER OR TUMOR CELLS WITH MICRORNA145

This application claims benefit under 35 U.S.C. 119(e) of U.S. Provisional Application No. 61/556,642, filed Nov. 7, 2011, the entire content of which is incorporated by reference herein.

FIELD OF THE INVENTION

The present invention relates to a method for treating a cancer or tumor; in particular, the present invention is directed to a method for treating a cancer or tumor in a subject with microRNA145.

BACKGROUND OF THE INVENTION

Understanding the molecular mechanisms of tumorigenesis in a cancer cell is crucial to developing therapeutic approaches and to improving patient survival. It is suggested in some studies that a subset of cancer cells with high self-renewal and stemness properties, cancer stem cells (CSCs), are the key contributor to chemoradioresistance and are responsible for tumor progression as well as recurrence after conventional therapy (Bao, et al. Nature 444(7120):756-60, 2006; and Clarke, et al. Cancer Res. 66(19):9339-44, 2006). CSC-specific targeting, which could improve therapeutic efficacies and increase the patient survival rate, has become a prospective direction for cancer therapy development.

MicroRNAs (miRNAs) are a diverse family of small RNA molecules that function as a crucial post-transcriptional regulatory mechanism in various cellular functions. MicroRNAs play pivotal roles in regulating most biological processes of both normal development and various diseases, including cancer (Esquela-Kerscher and Slack. Nat Rev Cancer 6(4): 259-69, 2006; and Sempere, et al. ScientificWorld Journal. 9:626-8, 2009). In tumors with downregulated or upregulated miRNAs, the use of miRNAs or anti-miRNAs, respectively, could be a therapy for inducing apoptosis and/or cell cycle arrest in cancer cells. For example, miR-26a expression is reduced in hepatocellular carcinomas, and the delivery of miR-26a using an adeno-associated virus (AAV) results in the inhibition of tumorigenesis in a murine liver cancer model (Kota, et al. Cell. 137(6):1005-17, 2009).

MicroRNA145 (miR145), is known as a tumor-suppressive miRNA, which is associated with tumor growth and metastasis in certain types of cancer (Michael, et al. Reduced accumulation of specific microRNAs in colorectal neoplasia. Mol Cancer Res. 1(12):882-91, 2003; Iorio, et al. MicroRNA signatures in human ovarian cancer. Cancer Res. 67(18):8699-707, 2007; Iorio, et al. MicroRNA gene expression deregulation in human breast cancer. Cancer Res. 65(16):7065-70, 2005; Akao, et al. Downregulation of microRNAs-143 and -145 in B-cell malignancies. Cancer Sci. 98(12):1914-20, 2007; and Schepeler, et al. Diagnostic and prognostic microRNAs in stage II colon cancer. Cancer Res. 68(15):6416-24, 2008). However, it is uncertain if miR145 is involved in other cancers and cancer stem cell properties.

BRIEF SUMMARY OF THE INVENTION

The present invention unexpectedly found that the expression of microRNA145 (miR145) was inversely correlated with the levels of Oct4 and Sox2 in GBM-CD133$^+$ cells and malignant glioma specimens, and negatively regulated GBM tumor growth. It was also confirmed in the present invention that miR145 in a delivery vehicle to brain tumor cells could significantly inhibited the tumorigenic and cancer stem cell-like properties. Moreover, the invention demonstrated that miR145 directly targeted the 3'UTR of SOX9 and ADAM17, thereby suppressing the tumor-initiating properties of head and neck cancer cells. Similarly, the delivery of miR145 attenuated tumor progression in vivo. Accordingly, the present invention provides a new approach for treating a cancer, particularly brain and/or head and neck cancer with miR145.

In one aspect, the present invention provides a method for inhibiting cancer stem cell like and chemoradioresistant properties of cancer or tumor cells comprising delivering miR145 to the cancer or tumor cells.

In another aspect, the invention provides a pharmaceutical composition for inhibiting cancer stem cell-like and chemoradioresistant properties of cancer or tumor cells comprising miR145.

Further provided is a method for treating a brain tumor comprising administering to a subject in need thereof a therapeutically effective amount of miR145 in a delivery vehicle, wherein such method may further comprise the treatment of radiotherapy and/or the administration of an anti-cancer drug, such as temozolomide, whereby a synergistically improved survival rate of the subject can be obtained.

Also provided is a method for treating head and neck cancer, comprising administering to a subject in need thereof a therapeutically effective amount of miR145, wherein the miR145 may be carried by a vector.

It is believed that a person of ordinary knowledge in the art where the present invention belongs can utilize the present invention to its broadest scope based on the descriptions herein with no need of further illustration. Therefore, the following descriptions should be understood as of demonstrative purpose instead of limitative in any way to the scope of the present invention.

BRIEF DESCRIPTION OF THE SEVERAL VIEWS OF THE DRAWINGS

For the purpose of illustrating the invention, there are shown in the drawings embodiments which are presently preferred. It should be understood, however, that the invention is not limited to the preferred embodiments shown in the drawings.

FIG. 1B provides the results of the soft agar colony formation assays on sphere-forming and non-sphere-forming cells isolated from five patient-derived GBM cells; FIGS. 1C and 1D respectively provide in vitro invasion and in vivo tumor-initiating abilities of CD133$^+$, CD133$^-$, SF$^+$, and SF$^-$ cells from patient-derived GBM specimens; and FIG. 1E provides the statistical analysis of the quantitative RT-PCR results showing a negative correlation between miR145 and both Sox2 and Oct4 (*P<0.05 vs. CD133$^-$ or SF$^-$).

FIG. 2B shows that after the preparation of the miR145-PU-PEI complexes, the cells were transfected by adding the complexes to the culture. The successful transfection was confirmed by RT-PCR and Western blot.

FIG. 3F provides the xenograft tumor volumes in all of the recipients monitored during the 6-week experimental period. Data shown here are the means±SD of six independent experiments (*P<0.05 vs. Parental).

FIG. 4 shows miR145-mediated downregulation of Oct-4 and Sox2 by directly targeting the Oct4 and Sox-2 3' UTRs; wherein FIG. 4A shows the construction of luciferase reporter plasmids containing wild-type (WT) or serial deleted forms (D1-D2) of the 3'UTRs of Sox2 and Oct4 (upper panel), and a luciferase reporter assay performed by co-transfecting the reporter plasmids with or without miR145 in GBM-CD133$^+$ cells (bottom panel); FIG. 4B shows the putative miR145 binding sites on the Sox2 and Oct4 3'UTRs, in which the sequences of the wild-type (WT) and mutated (Mut) miR145 binding sites designed for reporter plasmid construction are listed (upper panel); the effects of miR145 on wild-type (WT) or mutated (Mut) Sox2 and Oct4 3'UTRs were assessed by a luciferase activity assay (bottom panel); data shown are the mean±SD of 3 independent experiments; and FIG. 4C provides the results of Northern blots confirming the successful delivery of miR145 using the PU-PEI vector (upper left); and the results of Western blots showing that miR145 inhibits Sox2 and Oct4 protein production (lower left and right), in which the data are the mean±SD of six independent experiments (In FIG. 4A, *P<0.05 vs. PU-PEI control; in FIGS. 4B and 4C, *P<0.05 vs. Mock).

FIG. 5 shows that PU-PEI-mediated miR145 delivery repressed the stem-like gene expression signature of GBM-CSCs; wherein FIG. 5A shows that the indicated cells were subjected to gene expression microarray analysis (gene tree); the genes that were differentially expressed between each group are represented by a hierarchical heat map; each represented cell line was analyzed in triplicate; the time-dependent changes in the expression levels of the aforementioned genes are presented as a log scale of the expression values, provided by GeneSpring GX software; FIG. 5B provides the multidimensional scaling analysis illustrating the average lineage transcriptome distances among ESCs, MSCs, GBM-CD133$^+$, GBM-CD133$^+$/PU-PEI, GBM-CD133$^+$/PU-PEI-miR145, and GBM-CD133$^-$ cells, in which the PU-PEI-miR145 complex shifted the transcriptome distance of the GBM-CD133$^+$ cells from its parental cells toward the GBM-CD133$^-$ cells; FIG. 5C provides the effect of PU-PEI-mediated miR145 delivery on the percentage of GBM-CD133$^+$ cells; FIG. 5D provides the effect of PU-PEI-mediated miR145 delivery on the size of the side population in GBM-CD133$^+$ cells; and FIG. 5E provides the quantitative RT-PCR analysis of the mRNA expression levels of the stemness genes and the oncogene Bmi-1 after receiving PU-PEI-mediated miR145 delivery. Data shown here are the mean±SD of six independent experiments (*P<0.05 vs. Parental).

FIG. 6B shows the results of the MTT assay, in which after exposure to different doses of TMZ (left) or cisplatin (right), as indicated, the cell viability of the parental GBM-CD133$^+$ cells, the GBM-CD133$^+$ cells transfected with PU-PEI only, and the GBM-CD133$^+$ cells transfected with PU-PEI-miR145 were evaluated; FIGS. 6C and 6D provide the percentage of MDR$^+$ cells and ABCG2$^+$ cells, respectively, which was analyzed by flow cytometry; FIG. 6E provides the expression levels of the MDR genes, ABCG2, ABCB5, Bcl2, Bcl-xl and Bmi-1 in the cells indicated, which were determined by quantitative RT-PCR; FIG. 6F provides the results of Western blots showing that miR145 downregulates Bcl-2, Bcl-xl, and Bmi-1 and upregulates Bax; and FIG. 6G provides the results of the sphere formation assay (left) and the TUNEL assay (right) on patient-derived GBM-CD133$^+$ cells treated with irradiation and/or TMZ. Data shown here are the mean±SD of six independent experiments (*P<0.05 vs. Parental).

FIG. 7 shows that the PU-PEI-mediated miR145 delivery enhanced the efficacy of irradiation and TMZ on GBM tumorigenesis in orthotopic human GBM-CD133$^+$-transplanted immunocompromised mice; wherein FIGS. 7A and 7B show the effects of PU-PEI-miR145 on cyclosporine-treated immunosuppressive mice, in which the size of the tumors was monitored by bioluminescence imaging (BLI) every 7 days, up to 6 weeks; FIG. 7C provides ex vivo biopsy and gross necropsy findings demonstrating GBM tumor formation in the different treatment groups of xenotransplanted recipients (upper and middle panels); FIG. 7D provides the cumulative survival of the recipients receiving PU-PEI-miR145, ionizing radiation, and/or TMZ; and FIG. 7E provides quantitative RT-PCR analysis of the mRNA expression levels of the stemness genes and the oncogene Bmi-1 in the xenograft after receiving PU-PEI-miR145, ionizing radiation, and/or TMZ. Data shown here are the mean±SD of six independent experiments (*P<0.05 vs. PU-PEI control).

FIGS. 8B, 8C and 8D show the effects of miR145 knockdown on sphere formation, the activity of ALDH1, and the expression of CD44, respectively, in the indicated cells; FIG. 8E shows the effect of miR145 knockdown on tumor size in nude mice, which were subcutaneously transplanted with Spg-miR145 or Spg-ctrl transfected cells and monitored for 4 weeks for the occurrence of tumor mass; FIG. 8F shows the effects of miR145 knockdown on the number of invasive cells in which the number of invasive cells were calculated and presented in the graph as relative fold change in comparison to Spg-ctrl-transfected cells; and FIG. 8G shows the effects of miR145 knockdown on the number of metastatic tumor nodules in mice transplanted with the indicated cells through tail vein (Spg: SPONGE).

FIG. 9B provides miR145 target sites predicted in the 3'UTR regions of Sox9 and ADAM17 (top) and the constructed 3'UTR reporter plasmids of Sox9 and ADAM17 containing wild-type, mutated, and serial deleted forms of miR145 target sequences (bottom); FIG. 9C provides the results of the reporter assays performed in HNC-1 and HNC-2 cells with wild-type (WT) and mutated (Mut) reporter plasmids; FIG. 9D shows that ALDH$^+$CD44$^+$ cells derived from HNC-1 and HNC-2 were transfected with GFP-tagged miR145 (pLV-miR145) or empty vector (pLV), and the transfection efficiency and the mRNA expression level of miR145 were assessed by quantitative real-time PCR; FIG. 9E provides the protein expression levels of SOX9 and ADAM17 in miR145-transfected ALDH$^+$CD44$^+$ and Spg-miR145-transfected ALDH1$^-$CD44$^-$ cells, which were analyzed by western blot; FIG. 9F provides the results of western blot analysis of SOX9 and ADAM17 protein levels in ALDH$^+$ CD44$^+$ HNC cells subjected to concomitant knockdown of Sox9 and ADAM17; and FIG. 9G provides the occurrence of tumor mass and the tumor incidence in each group, in which NOD-SCID mice were subcutaneously injected with various numbers of PLV-, pLV-miR145-, sh-Luc-, and shSOX9+ shADAM17-transfected ALDH$^+$CD44$^+$ cells (from 100 to 100,000) derived from HNC-1, HNC-2, and FaDu (n=3), and were monitored for 4 to 12 weeks.

FIG. 11B is a panel of HNC patient samples from non-tumor and poorly differentiated tumor specimens, which was collected and immunohistochemically stained with anti-SOX9 and anti-ADAM17 antibodies; and FIG. 11C provides an overall survival correlation analysis performed for HNC patient samples expressing different levels of the indicated molecules.

DETAILED DESCRIPTION OF THE INVENTION

Figure 1:
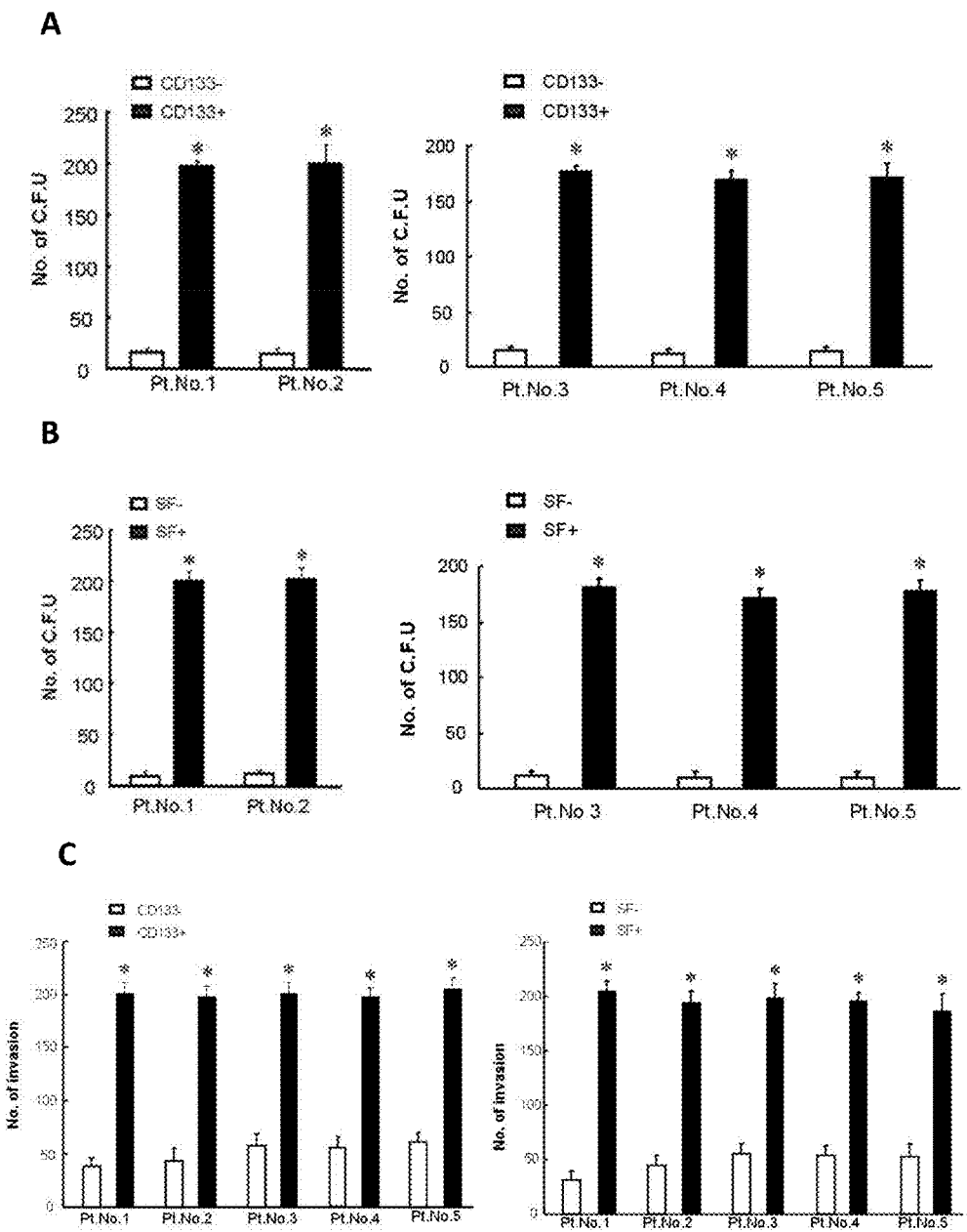
FIG. 1 shows low miR145 levels and high Sox2/Oct4 levels of in GBM-CSCs and high-grade glioma cells; wherein FIG. 1A provides results of the soft agar colony formation assays on CD133$^+$ and CD133$^-$ cells separated from five patient-derived GBM specimens by flow cytometry.

Unless defined otherwise, all technical and scientific terms used herein have the same meaning as commonly understood by a person skilled in the art to which this invention belongs. All publications mentioned herein are incorporated herein by reference to disclose and describe the methods and/or materials in connection with which the publications are cited.

As used herein, the singular forms "a", "an", and "the" include plural referents unless the context clearly dictates otherwise. Thus, for example, reference to "a sample" includes a plurality of such samples and equivalents thereof known to those skilled in the art.

In the present study, miRNA and mRNA microarray analyses with bioinformatics analyses were used to show that miR145 and its downstream targeted the stemness factors Sox2 and Oct4, had pivotal roles in mediating GBM malignancy. Accordingly, the effect of PU-PEI-mediated miR145 delivery on GBM malignancy was evaluated in GBM-derived CSCs, including GBM-CD133+ cells. The results suggested that PU-PEI-miR145 could effectively block CSC-like properties and improve chemoradioresistance in primary GBM-CD133$^+$ cells and orthotopic GBM-CD133$^+$-transplanted immunocompromised mice.

It was found that miR145 negatively regulated GBM tumor growth by directly targeting Oct4 and Sox2 in GBM-CD133$^+$ cells. The effect of polyurethane-short branch polyethylenimine-mediated miR145 (PU-PEI-miR145) was evaluated on GBM-CSCs. It was found that PU-PEI-miR145 delivery to GBM-CD133$^+$ cells significantly inhibited their tumorigenic and CSC-like abilities and facilitated their differentiation into CD133$^-$ non-CSCs. Furthermore, PU-PEI-miR145 delivery to GBM-CD133$^+$ cells effectively suppressed the expression of drug-resistance and anti-apoptotic genes and dramatically increased the sensitivity of the cells to radiation and chemotherapeutic drugs, including temozolomide. Finally, the in vivo delivery of PU-PEI-miR145 alone significantly suppressed tumorigenesis and synergistically improved the survival rate when used in combination with radiotherapy and temozolomide in orthotopic GBM-CD133$^+$ cell-transplanted immuno-compromised mice. Therefore, it was confirmed in the present invention that PU-PEI-miR145 is a potential therapeutic approach for malignant brain tumors.

In addition, we found that suppressing miR145 expression was also crucial for HNC-ALDH1$^+$CD44$^+$ cells to maintain their stem-like and cancer initiation capacities. In this regard, we identified 2 novel miR145 targets, SOX9 and ADAM17, which are directly inhibited via miR145 binding to their 3'UTR regions, and demonstrated that the overexpression of miR145 or the knockdown of SOX9 and ADAM17 suppressed the TICs properties of HNC-ALDH$^+$CD44$^+$ cells. Furthermore, we confirmed that in animal models, miR145 suppresses tumor initiation and growth via the inhibition of SOX9 and ADAM17. Finally, the miR145$^{low}$SOX9$^{high}$ADAM17$^{high}$ signature in patient tumor samples correlated with a poor survival rate. This is the first report demonstrating the regulatory role of the miR145-SOX9/ADAM17 signaling axis in the regulation of TICs properties in HNC.

Accordingly, the present invention provides a method for inhibiting cancer stem cell like and chemoradioresistant properties of cancer or tumor cells comprising delivering miR145 to the cancer or tumor cells, such as brain tumor cells and/or head and neck cancer cells.

In one embodiment of the invention, the miR145 is encapsulated by a delivery vehicle. In a certain example, the polymer is cationic polyurethane-short branch polyethylenimine (PU-sbPEI).

The present invention also provides a pharmaceutical composition for inhibiting cancer stem cell-like and chemoradioresistant properties of cancer or tumor cells comprising miR145.

The miR145 contained in the aforementioned pharmaceutical composition may be encapsulated in a PU-sbPEI or carried by a vector, including but not limited to a plasmid, cosmid, phagemid and a virus.

In one embodiment of the invention, the pharmaceutical composition further comprises a pharmaceutically acceptable carrier.

In further aspect, the present invention also provides a method for treating brain tumor comprising administering to a subject in need thereof a therapeutically effective amount of miR145 in a delivery vehicle, such as PU-sbPEI.

In certain embodiments, the method further comprises treating the subject with radiotherapy or anti-cancer drug. In a specific example, the anti-cancer drug is temozolomide.

In yet aspect, further provided is a method for treating head and neck cancer (HNC) comprising administering to a subject in need thereof a therapeutically effective amount of miR145, which may be carried by a vector selected from, e.g., a plasmid, cosmid, phagemid and a virus.

The present invention is further illustrated by the following examples, which are provided for the purpose of demonstration rather than limitation.

EXAMPLE

Materials and Methods

1. Isolation and Characterization of GBM-CD133$^+$ or GBM-CD133$^-$ Cell Subsets This research followed the tenets of the Declaration of Helsinki, and all samples were obtained after patients had given informed consent. The cells were dissociated from the samples of GBM patients and were labeled with 1 mL CD133/I micromagnetic beads per million cells using a CD133 cell isolation kit (Miltenyi Biotec, Bergisch Gladbach, Germany). CD133$^+$ or CD133$^-$ cells were plated onto 24-well culture dishes (5000 cells/well). The number of spheres was determined 10 days after plating cultured cells in serum-free DMEM/F12 medium (GIBCO, Grandlsland, N.Y., USA) that was supplemented with N2 supplement (R&D, Minneapolis, Minn., USA), 10 ng/mL human recombinant bFGF (R&D Minneapolis, Minn., USA), and 10 ng/mL EGF (R&D, Minneapolis, Minn., USA). For determining the percentage of CD133 surface marker, $1 \times 10^5$ cells were resuspended in 100 µL of PBS and incubated with anti-human CD133 (Miltenyi Biotec, Bergisch Gladbach, Germany) at 4° C. for 1 hour. After washing twice with PBS, labeled cells were resuspended in 100 µL of PBS with 1 µL of the FITC-conjugated goat anti-mouse IgG antibody (Chemicon, Temecula, Calif., USA) at 4° C. for 1 hour. Cells were then analyzed with a FACSCalibur apparatus (Becton-Dickinson, San Jose, Calif., USA).

2. Microarray Analysis and Bioinformatics

Total RNA was extracted from cells using Trizol reagent (Life Technologies, Bethesda, Md., USA) and the Qiagen RNAeasy (Qiagen, Valencia, Calif., USA) column for purification. Total RNA was reverse-transcribed with Superscript II RNase H-reverse transcriptase (Gibco BRL) to generate Cy3- and Cy5-labeled (Amersham Biosciences Co., Piscataway, N.J., USA) cDNA probes for the control and treated samples, respectively. The labeled probes were hybridized to a cDNA microarray containing 10,000 gene clone immobilized cDNA fragments. Fluorescence intensities of Cy3 and Cy5 targets were measured and scanned separately using a GenePix 4000B Array Scanner (Axon Instruments, Burlingame, Calif., USA). Data analysis was performed using GenePix Pro 3.0.5.56 (Axon Instruments, USA) and GeneSpring GX 7.3.1 software (Agilent, Palo Alto, Calif.). The average-linkage distance was used to assess the similarity between two groups of gene expression profiles as described below. The difference in distance between two groups of sample expression profiles to a third was assessed by comparing the corresponding average linkage distances (the mean of all pair-wise distances (linkages) between members of the two groups concerned). The error of such a comparison was estimated by combining the standard errors (the standard deviation of pair-wise linkages divided by the square root of the number of linkages) of the average-linkage distances involved. Classical multidimensional scaling (MDS) was performed using the standard function of the R program to provide a visual impression of how the various sample groups are related.

3. Synthesis of Polyurethane and Short Branch PU-PEI (PU-PEI)

L-lysine-diisocyanate (LDI) at the amount of 0.145 g (a) and N,N'-bis-(2-hydroxyethyl)-piperazine (PPA) at the amount of 0.1024 g (b) were respectively dissolved in 1 mL anhydrous DMF solvent and mixed in a three-neck reaction flask under a dry nitrogen purge, heated at 60° C. and allowed to react for 12 hrs using a 0.5 wt % dibutyltin dilaurate catalyst. Then an excess amount of methanol (4 ml) was slowly added into the reaction mixture until no unreacted isocyanate was detected. The polyurethane was precipitated and purified in ethyl ether and dried at 40° C. under vacuum. The polymers were characterized by FT-IR and $^1$H NMR. $^1$H-NMR (400 MHz, DMSOd$_6$, ppm) δ: 2.50-2.71 (—N$_2$(CH$_2$CH$_2$)$_2$), 2.99, 3.9 (—NCH$_2$CH$_2$O—), 3.12 (—NHCH(COOCH$_3$)CH$_2$—), 1,21-1.81 (6H, —CH(COOCH$_3$)CH$_2$CH$_2$CH$_2$CH$_2$—), 2.90 (—CH$_2$CH$_2$NH—), 3.67 (—NHCOOCH$_3$), 3.4 (—COOCH$_3$), 8.01 (—NHCH(COOCH$_3$)CH$_2$—), 3.51 (—CH$_2$NHCOOCH$_3$). PU-sbPEI was synthesized using the aminolysis reaction of polyurethane (c) and small branch PEI (MW=800) (sbPEI) in FIG. 2A. First, 0.1 g polyurethane was dissolved in 1 mL of anhydrous DMF and 0.6 g sbPEI (d) was dissolved in 0.5 mL MeOH with 1 mL Et3N. Two solutions were mixed slowly and allowed to react at 45° C. for at least 48 hrs. The polymer was precipitated in an excess amount of anhydrous ethyl ether. Purification was performed by re-dissolving the above polymer in 3 mL MeOH and precipitating in 4 mL three times before vacuum-dried at 40° C. The polymer (PU-sbPEI) (e) was further characterized by FTIR and $^1$H NMR.

4. Structural Characterization of PU and PU-sbPEI

The PU synthesized from LDI and PPA and the PU-sbPEI comprising PU and PEI were characterized by FT-IR and $^1$H NMR. FT-IR spectra of PU and PU-sbPEI all showed typical absorbance of urethane (1721-1732 cm-1, C═O stretching), (3351-3368 cm-1, N—H stretching); and absorbance of amide (1626-1638 cm-1, C═O stretching), (1516-1560 cm-1, N—H bending). $^1$H-NMR of PU (400 MHz, DMSOd$_6$, ppm): δ: 2.50-2.71 (—N$_2$(CH$_2$CH$_2$)$_2$), 2.99, 3.9 (—NCH$_2$CH$_2$O—), 3.12 (—NHCH(COOCH$_3$)CH$_2$—), 1,21-1.81 (6H, —CH(COOCH$_3$)CH$_2$CH$_2$CH$_2$CH$_2$—), 2.90 (—CH$_2$CH$_2$NH—), 3.67 (—NHCOOCH$_3$), 3.4 (—COOCH$_3$), 8.01 (—NHCH(COOCH$_3$)CH$_2$—), 3.51 (—CH$_2$NHCOOCH$_3$). $^1$H NMR of PU-sbPEI (400 MHz, D$_2$O, ppm):δ:2.48(—N$_2$(—CH$_2$—CH$_2$)$_2$), 2.91(—NCH$_2$CH$_2$O—), 3.99(—NCH$_2$CH$_2$O—), 4.35(—NHCH(CO—)CH$_2$—), 2.84, 1.32, 1.53 (—CHCH$_2$CH$_2$CH$_2$—), 2.91(—CH$_2$CH$_2$NH—), 3.56(—O—CH$_3$), 3.8(—CONHCH$_2$—), 2.48, 3.14(PEI:-CH$_2$—CH$_2$—), 3.51(—CH$_2$NHCOCH—), 8.01(—NHCH(CONH—)CH$_2$—), 0.95 (PEI:-NH—). The molecular weights of PU and PU-sbPEI were 15 kDa and 36 kDa, respectively measured by gel permeation chromatography. The percent of grafted PEI to PU was then calculated and showed 85% of the methyl ester from LDI blocks was conjugated.

5. Delivery of miR145 by PU-sbPEI

The microRNA-145 expression plasmid (pMiR145) was purchased from Addgene (Cambridge, USA). pMiR145 was dissolved in opti-MEM with final concentration 800 ng/µL. PU-PEI was dissolved in opti-MEM with final concentrations 2.4 µg/µL. pMiR145 and PU-PEI was mixed at a 1:1 ratio to reach the final concentration of 400 ng/µL of plasmid DNA and 1.2 µg/uL of PU-PEI to form the DNA-PU-PEI complexes. The complexes were then incubated at room temperature for 30 min. The miR-145 expression levels were further confirmed by PCR-based methods using miR-145 specific primers. For transfections, Cells were grown to about 70% confluency prior to transfection. The complexes were added directly to cells, and were removed at 6 hours post-transfection. Forty-eight hours later, cells were harvested and subjected for further experiments.

6. Constructions of Sox2 Oct4, Sox 9 and ADM17 3'UTR Site-Directed Mutagenesis Vectors All constructions were validated by sequencing. Oct4 Sox2, Sox 9 and ADM17 3'UTR were amplified from human cDNA by using following primer sets as listed below.

| Primers | Sequence (5' to 3') |
|---|---|
| Oct4 3'UTR forward | GGTGCCTGCCCTTCTAGGAATGGGG (SEQ ID NO: 1) |
| Oct4 3'UTR reverse | AAGTGTGTCTATCTACTGTGTCCCAGG (SEQ ID NO: 2) |
| Sox2 3'UTR forward | GGGCCGGACAGCGAACTGGAGGGGG (SEQ ID NO: 3) |
| Sox2 3'UTR reverse | CAGTGTCCATATTTCAAAAATTTATTTA (SEQ ID NO: 4) |
| Sox9 3'UTR forward | ATGCACTAGTGGAGGCCTCCCACGAAGGGCGAAGA (SEQ ID NO: 5) |
| Sox9 3'UTR reverse | ATGCGTTTAAACCTTTTTAATGCAATGTATATTTATT (SEQ ID NO: 6) |
| ADAM17 3'UTR forward | ATGCACTAGTTTTAGTTCTCAGCTCTTCTGACTTA (SEQ ID NO: 7) |
| ADAM17 3'UTR reverse | ATGCAAGCTTGAGGCAGAGTCTCACTCTGTCACCC (SEQ ID NO: 8) |

Human Oct4, Sox2, Sox9 and ADAM17 full length 3'UTR were cloned into pMIR luciferase report vectors. Point mutations in these genes were introduced by PCR-based site-directed mutagenesis method. The putative miR145 binding sites on the Oct4, Sox2, Sox9 and ADAM17 3'UTRs as well as the corresponding binding sequence on miR145 are listed below.

| | Target Sequence (5' to 3') |
|---|---|
| miR145 | GUCCAGUUUUCCCAGGAAUCCCU (SEQ ID NO: 9) |
| Oct4 3'UTR | AGGGGAGUUUGGGGCAACUGGUU (SEQ ID NO: 10) |
| mutOct4 3'UTR | AUUGGAGUUUUGUGCAAUUCUUU (SEQ ID NO: 11) |
| Sox2 3'UTR | GGCCGGACAGCGAACUGGAG (SEQ ID NO: 12) |
| mutSox2 3'UTR | GGCGGAACAGCGCGCUAAAG (SEQ ID NO: 13) |
| Sox9 3'UTR | UUUUUGUUGAAAACAAACUGGAA (SEQ ID NO: 14) |
| mutSox9 3'UTR | UUUUUGUUGAAAACACAGUAGCA (SEQ ID NO: 15) |
| ADAM17 3'UTR | UUUAUUUGUGAUGACAACUGGAA (SEQ ID NO: 16) |
| mutADAM17 3'UTR | UUUAUUUGUGAUGACAGAUCGCA (SEQ ID NO: 17) |

Other primer and target sequences used in this invention are given below:

| Primers for wild type sequence and deletion mutants of 3'UTR | | |
|---|---|---|
| SOX9 3'UTR | SOX9-WT-F | 5'-ATGCACTAGTGGAGGCCTCCCACGAAGGGCGAAGA-3' (SEQ ID NO: 5) |
| | SOX9-D1 | 5'-ATGCGTTTAAACCCACACACACACACAATATAAGGCA-3' (SEQ ID NO: 18) |
| | SOX9-D2 | 5'-ATGCGTTTAAACCGGGGGCAGTGTGCTCGGGCACTTA-3' (SEQ ID NO: 19) |
| | SOX9-D3 | 5'-ATGCGTTTAAACTTTATCTAAAAATATGTATAAATCC-3' (SEQ ID NO: 20) |
| | SOX9-WT-R | 5'-ATGCGTTTAAACCTTTTTAATGCAATGTATATTTATT-3' (SEQ ID NO: 6) |
| ADAM17 3'UTR | ADAM17-WT-F | 5'-ATGCACTAGTTTTAGTTCTCAGCTCTTCTGACTTA-3' (SEQ ID NO: 7) |
| | ADAM17-D1 | 5'-ATGCAAGCTTAATTCAACTGGCTACCATGTAGC-3' (SEQ ID NO: 21) |
| | ADAM17-D2 | 5'-ATGCAAGCTTCAAAAAAAAAAAAAAAAAAAAAAC-3' (SEQ ID NO: 22) |
| | ADAM17-D3 | 5'-ATGCAAGCTTAAAACCTGAAAGCCTCAAAATAAGC-3' (SEQ ID NO: 23) |
| | ADAM17-WT-R | 5'-ATGCAAGCTTGAGGCAGAGTCTCACTCTGTCACCC-3' (SEQ ID NO: 8) |
| Primers for Sponge and Antisense of miR145 and Scramble constructions | | |
| SPONGE FORWARD | | 5'-GATCCAGGGATTCCTCCCAAACTGGACAGATCTGGCCGCAC-3' (SEQ ID NO: 24) |
| SPONGE REVERSE | | 5'-TCGAGTGCGGCCAGATCTGTCCAGTTTGGGAGGAATCCCTG-3' (SEQ ID NO: 25) |
| SCRAMBLE FORWARD | | 5'-GATCCCATTAATGTCGGACAACTCAATCAGATCTGGCCGCAC-3' (SEQ ID NO: 26) |
| SCRAMBLE REVERSE | | 5'-TCGAGTGCGGCCAGATCTGATTGAGTTGTCCGACACATTAATGG-3' (SEQ ID NO: 27) |
| Target Sequence of lentiviral-Based Sh-RNA | | |
| Target Sequence for Sox9-knockdown (Sh-RNA) | | |
| Target Sequence | | 5'-GCGGAGGAAGTCGGTGAAGAA-3' (SEQ ID NO: 28) |
| Target Sequence for ADAM17-knockdown (Sh-RNA) | | |
| Target Sequence | | 5'-CCTATGTCGATGCTGAACAAA-3' (SEQ ID NO: 29) |

7. Side Population Analysis

Cells were resuspended at 1×106/mL in pre-warmed DMEM with 2% FCS. Hoechst 33342 dye was added at a final concentration of 5 µg/mL in the presence or absence of verapmil (50 µM; Sigma) and was incubated at 37° C. for 90 min with intermittent shaking. At the end of the incubation, the cells were washed with ice-cold HBSS with 2% FCS and centrifuged down at 4° C., and resuspended in ice-cold HBSS containing 2% FCS. Propidium iodide at a final concentration of 2 µg/mL was added to the cells to gate viable cells. The cells were filtered through a 40-µm cell strainer to obtain single cell suspension before analysis. The Hoechst 33342 dye was excited at 357 nm and its fluorescence was dual-wavelength analyzed (blue, 402-446 nm; red, 650-670 nm). Analyses were done on FACSAria (BD, San Diego, Calif.).

8. Radiation Treatment and Clonogenic Assay

Ionizing irradiation (IR) was delivered from a Theratronic T-1000 cobalt unit (Theratronic Internation, Inc., Ottawa, Canada) at a dose rate of 1.1 Gy/min (SSD=57.5 cm). Briefly, cells in the control and irradiated groups were exposed to different radiation dosages (0, 2, 4, 6, 8, and 10 Gy). After incubating for 10 days, colonies (>50 cells per colony) were fixed and stained for 20 minutes with a solution containing crystal violet and methanol. Cell survival was determined by a colony formation assay. Plating efficiency (PE) and survival fraction (SF) were calculated as follows: PE=(colony number/number of inoculated cells)×100%; SF=colonies counted/(cells seeded×[PE/100]).

9. Bioluminescence Imaging (BLI)

All procedures involving animals were in accordance with the institutional animal welfare guidelines of the Taipei Veterans General Hospital. Eight-week-old nude mice (BALB/c strain) were injected with different number of cells orthotopically BLI was performed using an IVIS50 animal imaging system (Xenogen Corp.). The photons emitted from the target site penetrated through the mammalian tissue and could be externally detected and quantified using a sensitive light-imaging system. The image acquisition time was 1 min. The displayed images of the tumor sites were drawn around and quantified in photons per second using Living Image software (Xenogen Corp.). The volume was calculated (according to the following formula: [length×width2]/2), and then analyzed using Image-Pro Plus software.

10. Statistical Analysis

Results are reported as mean ±SD. Statistical analysis was performed using Student's t test or a one-way or two-way analysis of variance (ANOVA) followed by Turkey's test, as appropriate. The survival rate analysis was performed using log-rank test. Results were considered statistically significant at $P<0.05$.

Results

1. Downregulation of miR145 in GBM Patients

Recent studies have suggested that the aggressiveness of GBMs may be attributed to the persistence of CSCs. Lee et al. have shown that GBM tumor stem cells, or CSCs, are a more reliable model for understanding the biology of GBMs than other commonly used GBM cell lines because CSCs more closely minor the phenotype and genotype of primary tumors (Lee et al. Cancer Cell 2006; 9(5):391-403). GBM-associated CSCs (GBM-CSCs) can be cultured and enriched in suspension to generate floating spheroid-like bodies (SBs) and maintain their self-renewal capabilities in serum-free media with basic fibroblast growth factor (bFGF) and epidermal growth factor (EGF). Several studies have identified CD133 as a marker for brain tumor-initiating cells because $CD133^+$ cells from brain tumor biopsy specimens were able to initiate brain cancer in immunocompromised mice. We previously reported that $CD133^+$ cells isolated from an atypical teratoid/rhabdoid malignant pediatric brain tumor have CSC-like properties and are resistant to radiotherapeutic treatment. In line with the findings and rationale in these studies, we further designed single-walled carbon nanotubes that were conjugated with CD133 monoclonal antibodies. Combined with irradiation treatment, these nanotube-conjugated monoclonal antibodies selectively targeted and eradicated $CD133^+$ GBM cells. In the present study, we enriched the GBM-CSCs by isolating two subpopulations of primary GBM cells derived from 5 patient specimens (Pt. No. 1-5); these subpopulations included $CD133^+$ cells ($GBM-CD133^+$, FIG. 1A) and sphere-forming cells grown in serum-free culture conditions ($GBM-SF^+$, FIG. 1B). Soft agar colony assays indicated that the $GBM-CD133^+$ cells consistently exhibited higher tumorigenicity than did the $GBM-CD133^-$ cells, and the GBM-SF+ cells also exhibited more prominent tumorigenicity than did the GBM-SF− cells (FIG. 1A-B). The CSC-like properties of the $GBM-CD133^+$ and $GBM-SF^+$ cells were also validated by their in vitro invasion (FIG. 1C) and in vivo tumor-initiating abilities (FIG. 1D). These four subpopulations of GBM cells, i.e., $GBM-CD133^+$, $GBM-CD133^-$, $GBM-SF^+$, and $GBM-SF^-$, were subjected to miRNA and mRNA microarray analyses to attempt to identify the GBM-CSC-specific mechanisms that mediate GBM malignancy. miRNAs or genes that were either upregulated more than 2-fold or downregulated more than 50% were assessed. We then used a literature-based comparison and on-line target scan prediction software (Targetscan program, www.targetscan.org) to identify consistently up- or down-regulated signaling pathways in both databases. miR145 and its downstream targets Sox2 and Oct4 were selected for further investigation by the Targetscan program. This selection was further validated by quantitative RT-PCR, which compared the expression levels of miR145, Sox2, and Oct4 between the $GBM-SF^+$ and $GBM-SF^-$ cells and between the $GBM-CD133^+$ and $GBM-CD133^-$ cells from patient-derived GBM specimens (FIG. 1E). In the $GBM-SF^+$ and $GBM-CD133^+$ cells, the miR145 level was low, while Oct4 and Sox expression were high; an inverse pattern of miR145, Oct4 and Sox gene expression was observed in the GBM-SF− and $GBM-CD133^-$ cells (FIG. 1E). Remarkably, the statistical analysis of the mRNA expression of these genes from the 5 patient-derived GBM specimens predicted a strong negative correlation between miR145 and downstream Oct4 or Sox2 in the $GBM-SF^+$ and $GBM-CD133^+$ cells (FIG. 1E, bottom panel). Consistent with these data, we found a similar pattern of miR145 downregulation and Sox2/Oct4 upregulation in clinical biopsy tissues from patients with high-grade gliomas and GBMs relative to the mRNA levels in the samples from patients with low-grade tumors. An inverse pattern was observed in low-grade gliomas (data not shown). Taken together, our data indicated that the downregulation of miR145 is accompanied by an upregulation of Sox2 and Oct4 in GBM-associated CSCs and high-grade GBMs, in which miR145 and these sternness factors may play pivotal roles in mediating GBM malignancy.

2. Structural Characterizations of PU-PEI

Figure 2:
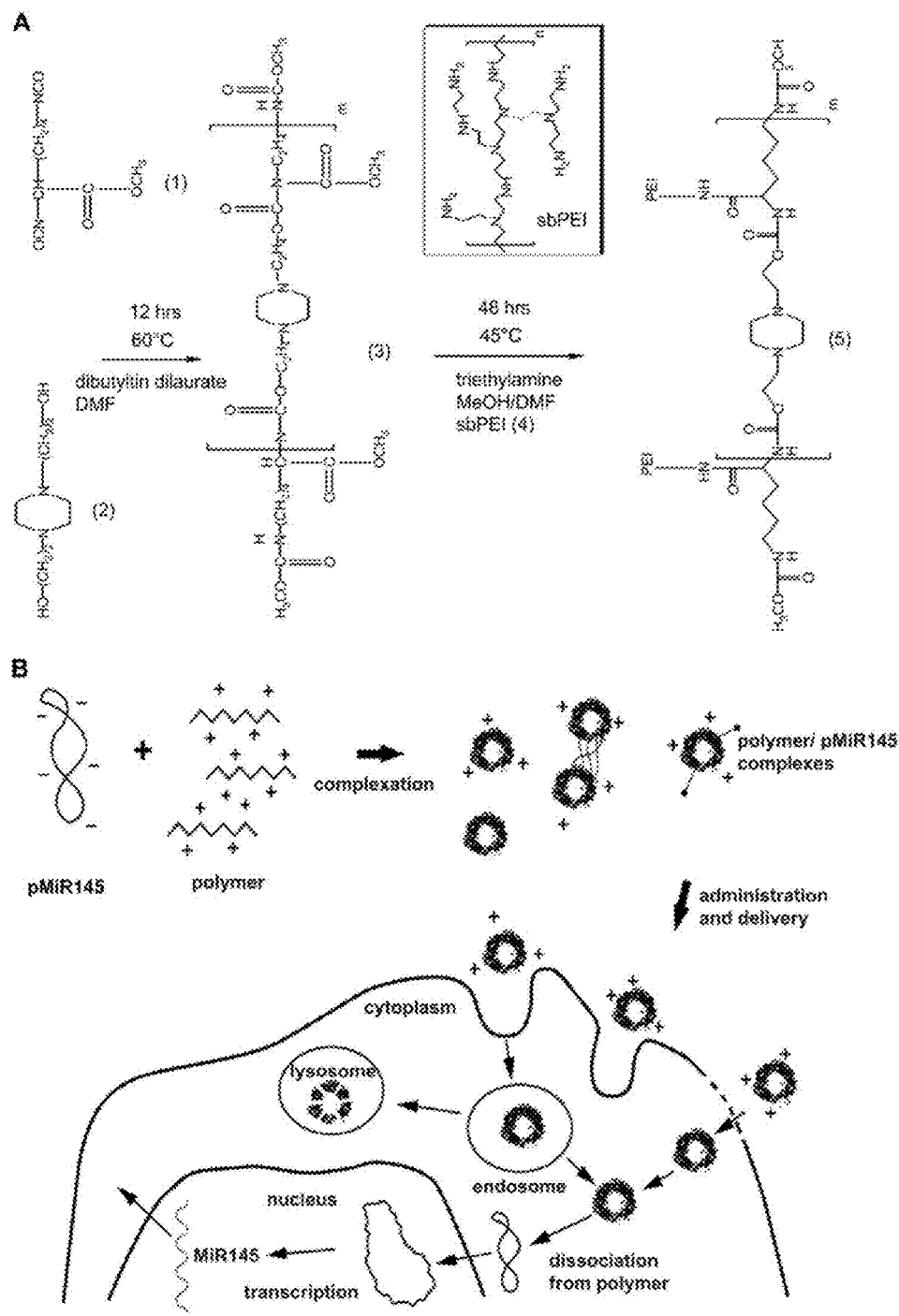
FIG. 2 provides a schematic diagram showing PU-PEI synthesis and PU-PEI-mediated delivery of miR145 into cells; wherein FIG. 2A provides the synthesis of PU-PEI.

Because lower miR145 levels and higher sternness factors levels were detected in GBM-derived CSCs (including $GBM-CSC^+$ and $GBM-SF^+$) and in high-grade GBMs, we investigated the potential rescuing role of miR145 by overexpressing miR145 in $GBM-CD133^+$ cells in serum-free cultured media (also denoted as GBM-CSCs). PU-PEI is not cytotoxic and has a high transfection efficiency, and thus PU-PEI was used here as a non-viral delivery system to transfer miR145 into GBM-CSCs. The steps in the synthesis of PU-PEI are shown in FIG. 2A. After formation of polymer/miR145 complexes, the complexes were then delivered into GBM-CSCs. A schematic figure of PU-PEI-mediated miR145 gene delivery is shown in FIG. 2B.

3. Effects of PU-PEI-Mediated miR145 Delivery

To investigate the role of miR145 in the progression of GBM-CSCs, we first tested the delivery efficacy of miR145 using a GFP-conjugated PU-PEI-based system in two stable clones of patient-derived GBM-CSCs, GBM-CD133$^+$/#1 and GBM-CD133$^+$/#2 (FIG. 3A); these clones were cultured in serum-free media. Empty vector-delivered GBM-CSCs were produced simultaneously as controls. The microscopic GFP signal showed that PU-PEI-miR145 was successfully delivered to more than 90% of the GBM-CD133$^+$ cells. Compared to the parental and PU-PEI vector controls, PU-PEI-mediated miR145 delivery inhibited the proliferation rate (FIG. 3A), the invasiveness (FIG. 3B) and the number of soft agar colonies (FIG. 3C) in the two patient-derived GBM-CSCs. At the same time, these miR145-transfected GBM-CD133$^+$ cells lost their sphere-forming ability; miR145 transfection also caused the secondary and tertiary spheres to lose their sphere-forming ability (FIG. 3D). A similar inhibitory effect of PU-PEI-miR145 on in vitro migration was also found in both GBM-CD133$^+$/#1 and GBM-CD133$^+$/#2 (FIG. 3E). Furthermore, pretreatment with PU-PEI-miR145 reduced xenograft tumor growth in immunocompromised BALB/c nude mice (FIG. 3H). Taken together, these findings demonstrated the ability of PU-PEI-mediated miR145 delivery to suppress tumorigenesis in GBM-CD133$^+$ cells.

4. miR145 Directly Targets Sox2 and Oct4

Figure 4:
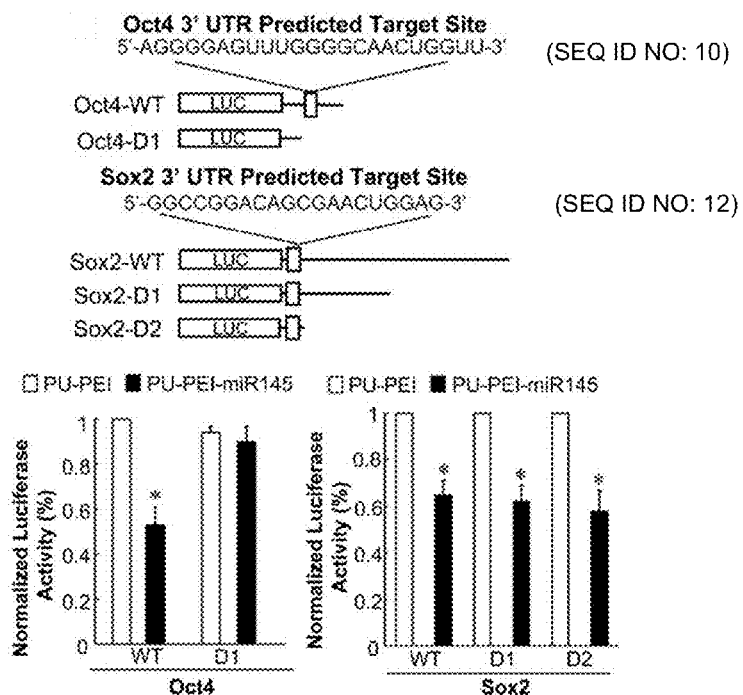
Figure 4:
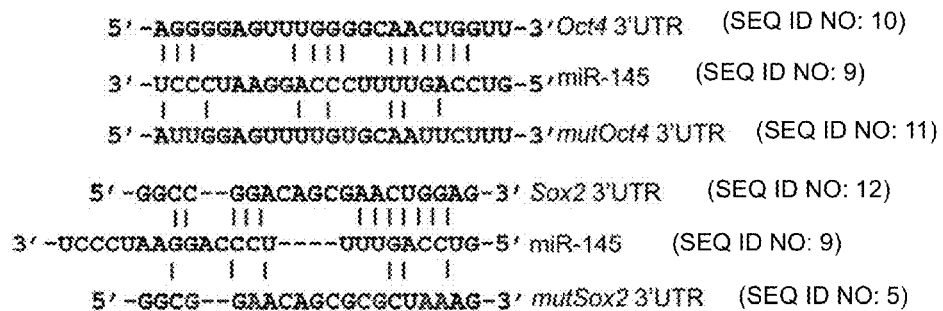
Figure 4:
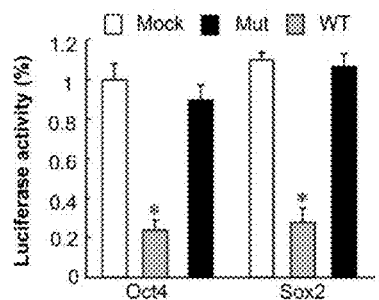

We searched the NCI60 tumor database (a dataset of gene expression and miRNA profiles of 60 National Cancer Institute cell lines) and screened for targets whose expression levels were negatively correlated with that of miR145. Compared to the other cell lines in the NC160 database, there was an inverse pattern of expression between miR145 and its downstream targets Sox2 and Oct4 in the brain tumor cell lines in the database, i.e., both Oct4 and Sox2 were upregulated while miR145 was downregulated. This inverse relationship between miR145 and Sox2/Oct4 might arise if miR145 directly inhibits the expression of its downstream targets. In ESCs, miR145 directly targets the 3'UTRs of the stemness factors Oct4, Sox2, and Klf4, resulting in decreased pluripotency. However, the regulation between miR145 and Sox2/Oct4 has not been investigated in GBM cells. We constructed luciferase reporter plasmids containing wild-type (WT) or serial-deleted forms (D1-D2) of the 3'UTRs of Sox2 and Oct4 (FIG. 4A, upper panel). The luciferase reporter assay was performed by co-transfecting the reporter plasmids either with or without miR145 in the GBM-CD133$^+$ cells. The results indicated that miR145 mediated the downregulation of Oct-4 and Sox2 by directly targeting the Oct4 and Sox-2 3' UTRs (FIG. 4A, lower panel). We then constructed luciferase reporter plasmids containing wild-type (WT) or mutated (Mut) miR145-targeting regions of Sox2 and Oct4 (FIG. 4B, upper panel). The luciferase reporter assay was performed by co-transfecting the reporter plasmids with PU-PEI-miR145 in the GBM-CD133$^+$ cells. miR145 inhibited the luciferase activity of the reporter plasmids containing the wild-type targeting site but not the mutated site, indicating that miR145 directly targets the 3'UTRs of Sox2 and Oct4 in GBM-CSCs (FIG. 4B, lower panel). Furthermore, Northern blot analysis revealed the successful delivery of miR145 into GBM-CSCs (FIG. 4C, left). Western blot analysis further confirmed the inhibitory role of miR145 on the protein expression of Sox2 and Oct4 in GBM-CSCs (FIG. 4C, left). The quantification of these blots indicated that Sox2 and Oct4 protein expression was consistently downregulated by miR145 delivery in the GBM-CSCs from two patients (FIG. 4C, right). These results validated the signal transduction of miR145 and it downstream targets Sox2 and Oct4.

5. Reduction of CSC-Like Properties by miR145

Figure 3:
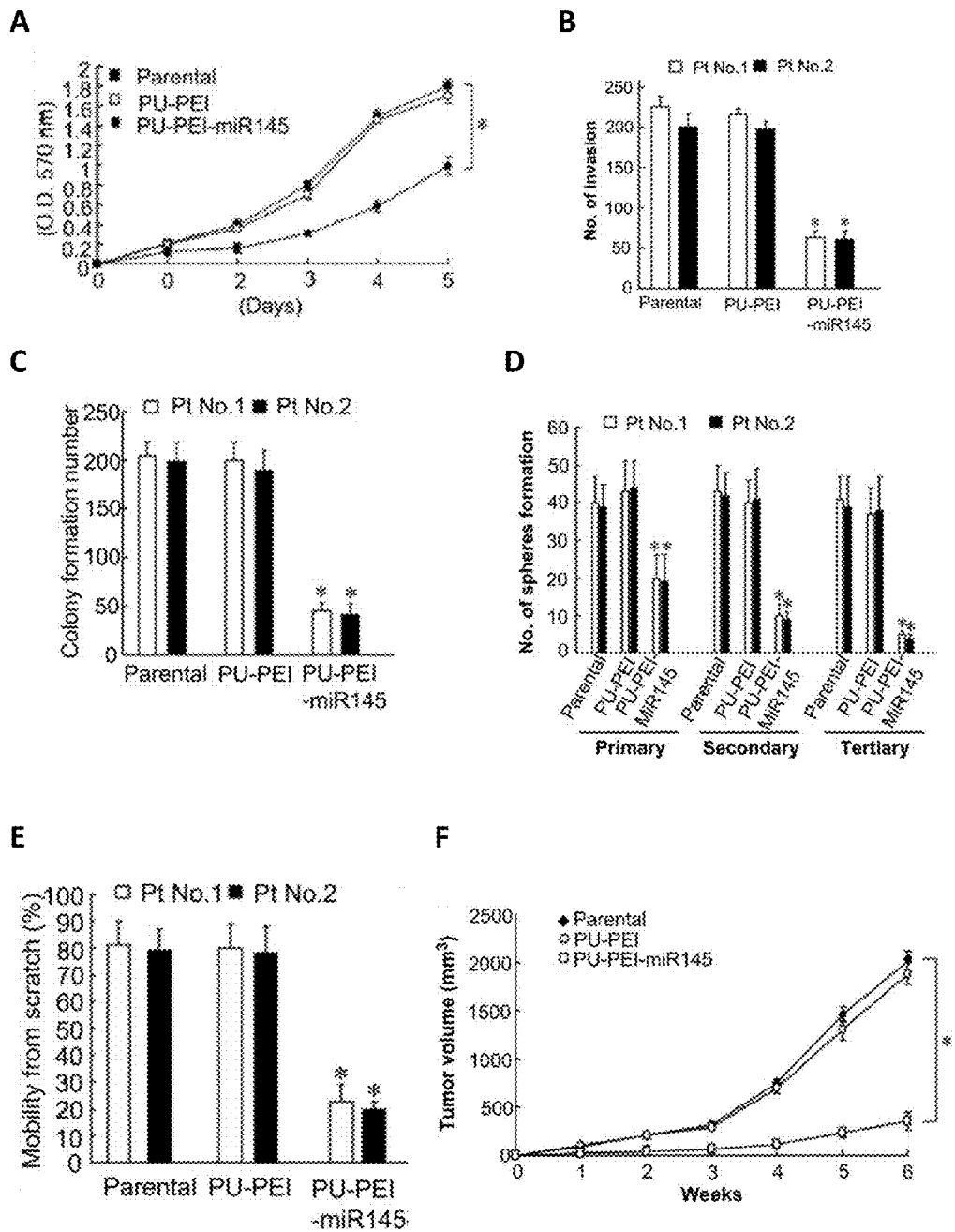
FIG. 3 shows that PU-PEI-mediated miR145 delivery reduced the GBM-CSC population; wherein FIGS. 3A, 3B, 3C, 3D and 3E provide the results of the proliferation assay, the cell invasion assay, the soft agar assay, the sphere formation assay, and the cell mobility assay on GBM-CD133$^+$ cells, respectively.
Figure 5:
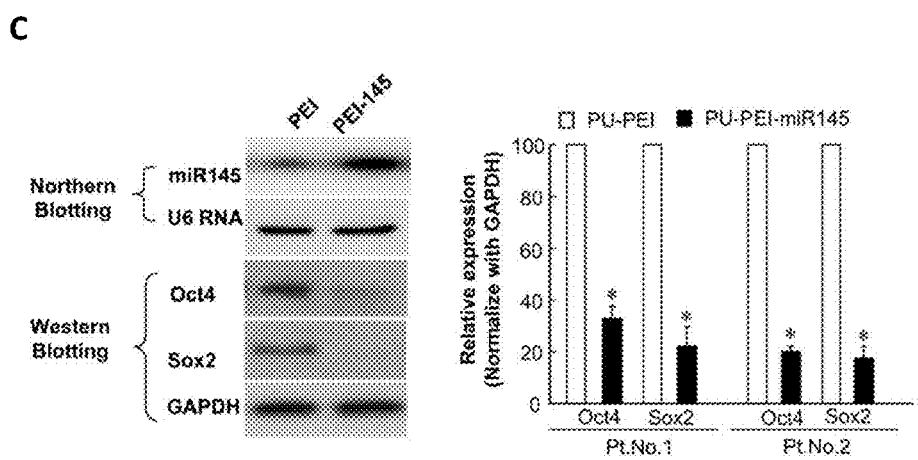
Figure 5:
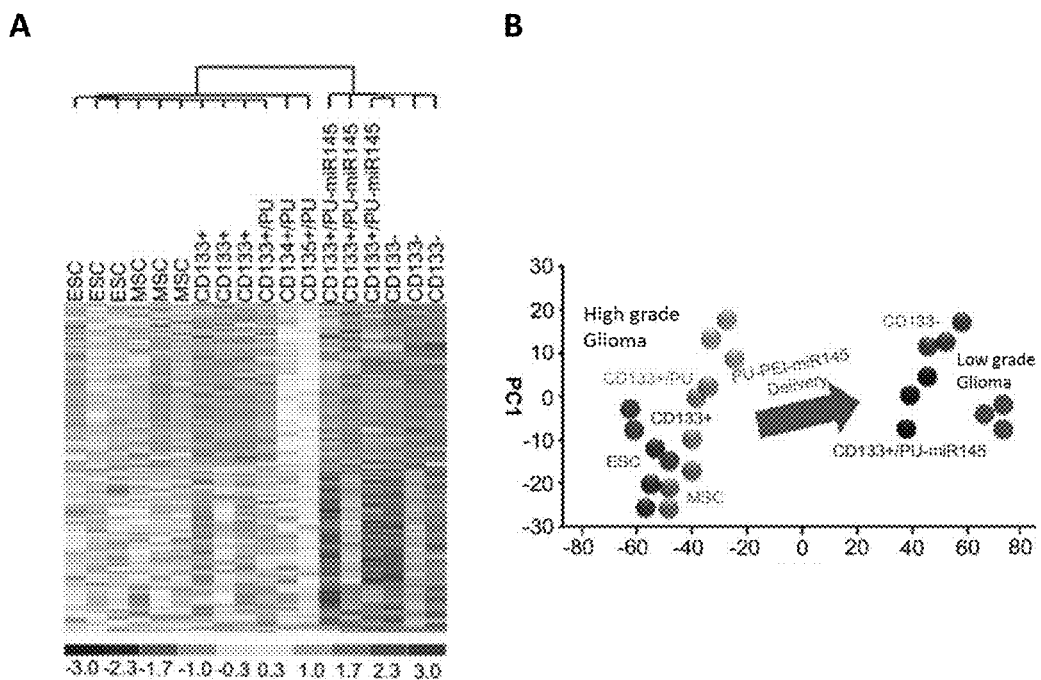

The loss of the tumor-initiating property in the PU-PEI-miR145-transfected GBM-CD133$^+$ cells (GBM-CD133$^+$/PU-PEI-miR145) implies that these cells are less stem-like than the parental cells (FIG. 3). We used a gene expression microarray to analyze the genomic traits of the GBM-CD133$^-$, GBM-CD133$^+$, GBM-CD133$^+$/PU-PEI, and GBM-CD133$^+$/PU-PEI-miR145 cell lines, along with ESCs. The results were entered into the Gene Ontology (GO) database search to find statistically represented functional groups. Consistent with the more prominent tumor-initiating and CSC-like properties of the GBM-CD133$^+$ cells, their gene expression pattern was similar to that of ESCs but different from that of GBM-CD133$^-$ cells (FIG. 5A). Interestingly, PU-PEI-mediated miR145 delivery (GBM-CD133$^+$/PU-PEI-miR145) shifted the stem cell-like gene expression patterns of the GBM-CD133$^+$ cells into a pattern close to that of the GBM-CD133$^-$ cells (FIG. 5A). The predominant processes downregulated in GBM-CD133+/PU-PEI-miR145 cells include those pertaining to mitosis, nuclear division, translation, Wnt signaling, and cell cycle regulation; processes related to growth regulation, cell adhesion, and the immune response were upregulated in these cells. Multidimensional scaling analysis further revealed that the gene expression patterns of the GBM-CD133$^+$ cells resembled the expression patterns of high-grade GBMs, ESCs and mesenchymal stem cells (MSCs) (FIG. 5B). PU-PEI-mediated miR145 delivery changed the gene expression pattern of the GBM-CD133$^+$ cells to one closer to that of the GBM-CD133$^-$ and low-grade GBM cells than that of the parental GBM-CD133$^+$ or GBM-CD133$^+$/PU-PEI cells (FIG. 5B). In addition, we used a literature-based network analysis of all MEDLINE records (titles and abstracts) and the Cytoscape open-source bioinformatics software platform to group the target-linkage genes from our microarray data. We found that the network genes that were involved in pathways related to stemness factors, including Sox2 and Oct4, and several drug-resistance genes from the ATP-binding cassette (ABC) transporter family are involved in parental GBM-CD133$^+$ cells but not in PU-PEI-miR145-transfected GBM-CD133$^+$ cells (GBM-CD133+/PU-PEI-miR145). Flow cytometry analysis of the CD133 surface marker indicated that PU-PEI-mediated miR145 delivery reduced the percentage of CD133$^+$ cells (FIG. 5C). In addition, miR145 delivery reduced the size of the side population from 5-6% to less than 1% in both GBM-CD133$^+$ clones (FIG. 5D). Furthermore, quantitative RT-PCR analysis confirmed that, in addition to Oct4 and Sox2, the expression of other stemness genes, including Nanog, c-Myc, and the oncogene Bmi1, were substantially attenuated by PU-PEI-mediated miR145 delivery (FIG. 5E). These data demonstrate that the overexpression of miR145 reduces CSC-like properties in GBMs.

6. Enhanced Chemoradiosensitivity by miR145

Figure 6:
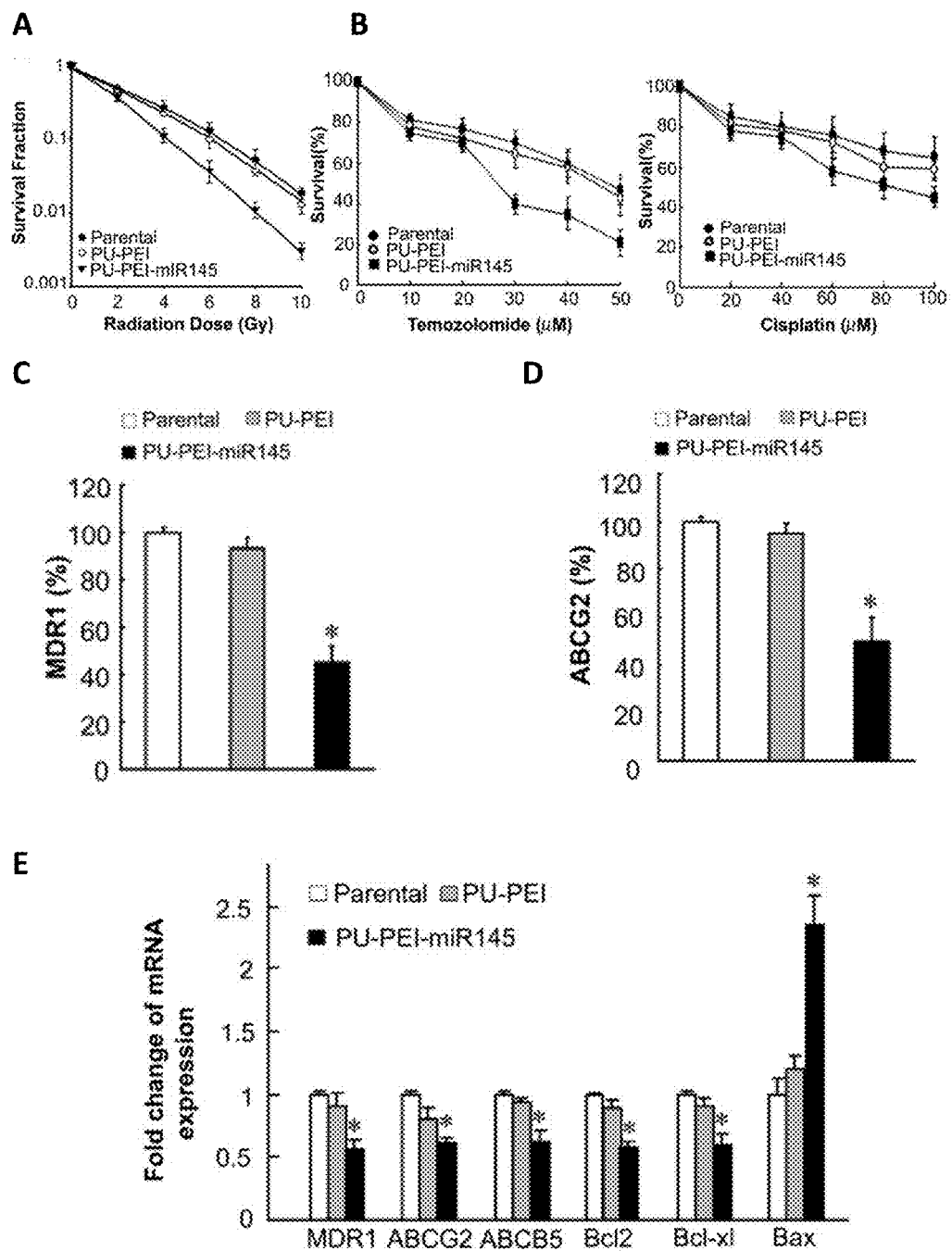
FIG. 6 shows that PU-PEI-mediated miR145 delivery enhanced the chemoradiosensitivity of GBM-CD133$^+$ cells to chemotherapeutic drugs; wherein FIG. 6A provides the evaluation of surviving cell fractions of the parental GBM-CD133$^+$ cells, the GBM-CD133$^+$ cells transfected with PU-PEI only, and the GBM-CD133$^+$ cells transfected with PU-PEI-miR145 after exposure to 2-10 Gy of irradiation.

The observation of miR145- and Sox2/Oct4-mediated regulation of the CSC population and its properties suggested their involvement in modulating the chemo- and radio-resistance of GBM-CSCs. Cell viability was measured to evaluate the sensitivity of the GBM-CD133$^+$ cells to radiation or chemotherapeutic drugs. Notably, GBM-CD133$^+$/PU-PEI-miR145 cells had the lowest survival fraction at all given radiation doses than the parental GBM-CD133$^+$ or GBM-CD133$^+$/PU-PEI cells, indicating that PU-PEI-mediated miR145 delivery enhanced radio-sensitivity in GBM-CD133$^+$ cells (FIG. 6A). In addition, GBM-CD133$^+$/PU- PEI-miR145 cells were also more sensitive to chemotherapeutic agents, including temozolomide (TMZ) and cisplatin (FIG. 6B), than the parental or vector control cells. The ABC (ATP-binding cassette) transporter family, including ABCB1 (also known as MDR1), ABCG2, and ABCG5, is associated with chemoresistance in cancers. We therefore tested the effect of PU-PEI-mediated miR145 delivery on a panel of ABC transporters. Flow cytometry analysis of MDR1 and ABCG2 indicated that PU-PEI-mediated miR145 delivery decreased the percentage of cells with a high expression of MDR1-positive or ABCG2-positive cells (FIGS. 6C and 6D). Remarkably, quantitative RT-PCR analysis showed that PU-PEI-mediated miR145 overexpression potentially suppressed the mRNA expression levels of MDR1, ABCG2, and ABCB5 (FIG. 6E). Bcl-2 and Bax are members of a family of cytoplasmic proteins that regulate apoptosis, in which Bcl-2 acts to inhibit apoptosis, whereas Bax counteracts this effect. In addition to enhancing the sensitivity to chemotherapy and downregulating drug-resistant genes, PU-PEI-mediated miR145 delivery suppressed the anti-apoptotic genes Bcl-2 and Bcl-xl but elevated the Bax gene (FIG. 6E). These results were confirmed at the protein level by Western blotting (FIG. 6F). Furthermore we found that miR145 delivery showed a suppressive effect on the sphere formation, and dramatically, this miR145 delivery further enhanced the suppressive effect of radiation or TMZ on sphere formation (FIG. 6G, left). Similar synergistic effects were also observed in the mean number of TUNEL-positive cells per high-power field in treated cells from different groups (FIG. 6G, right). These results indicated that the chemo- and radioresistance in the GBM-CD133$^+$ cells arose from decreased miR145 levels and the increased expression of several drug-resistant genes; the delivery of miR145 conversely enhanced chemo- and radioresistance, reduced drug-resistant gene expression and enhanced apoptotic activity. Taken together, PU-PEI-based miR145 delivery exhibited a prominent therapeutic effect in enhancing the sensitivity of chemoradiotherapy in GBM and GBM-CSCs.

7. In vivo Tumor Repression by miR145

Figure 7:
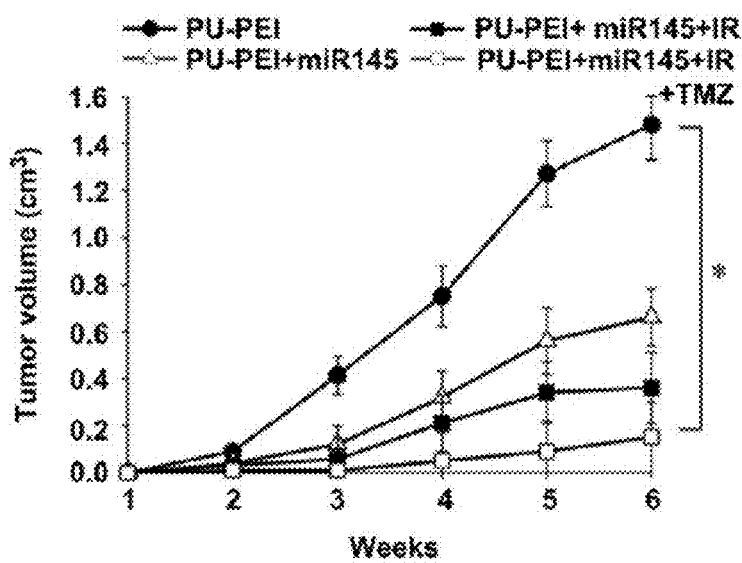
Figure 7:
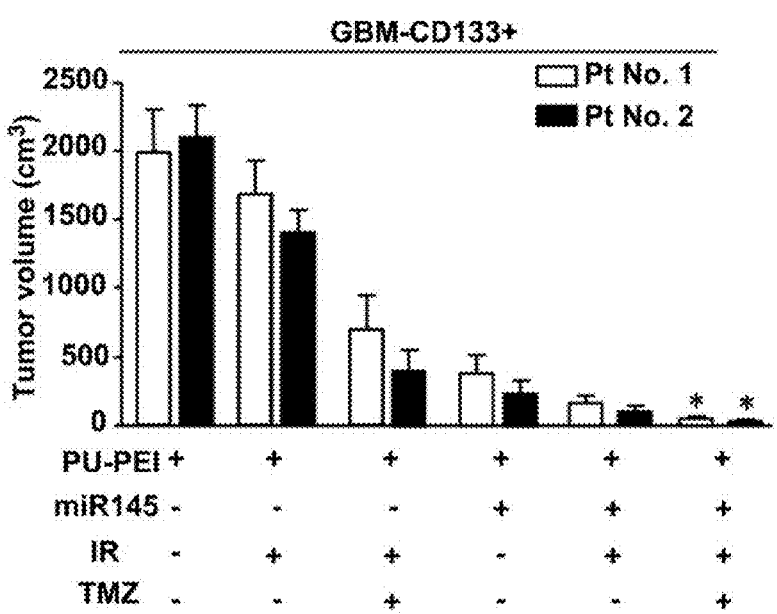

Based upon the in vitro findings, the therapeutic potential of the PU-PEI-miR145 complex against GBMs in vivo was investigated. We established a GBM tumor model and assessed the effects of miR145 delivery in this model. Briefly, cyclosporine-treated C57BL/6 mice were intra-cranially transplanted with $10^5$ patient-derived GBM-CD133$^+$ cells, and the size of the tumors was monitored every 7 days for up to 6 weeks. Five days after the xenotransplantation of the tumor cells, PU-PEI or PU-PEI-miR145 was intra-cranially delivered into the mice, which were then subjected to ionizing radiation (IR) and chemotherapeutic drugs. The tumor volume was continuously monitored by bioluminescence imaging. Severe tumor formation was observed in all of the recipients of the GBM-CD133$^+$ cells. Notably, PU-PEI-mediated delivery of miR145 largely reduced the tumor size, and co-treatment with IR led to a further reduction in tumor size (FIG. 7A). More importantly, miR145 delivery with a combination of radiotherapy and TMZ almost eliminated tumor formation during the experiment (FIG. 7A). Quantification of bioluminescence imaging at 6 weeks post-tumor transplantation confirmed that the maximal tumor repression was observed when a combination of PU-PEI-mediated miR145 delivery, radiotherapy, and TMX administration was used (FIG. 7B). As shown in Table 1, GBM-CD133$^+$ cells were isolated from 5 GBM patients, and the tumorigenic potential of the xenotransplanted GBM-CD133$^+$ cells was monitored. The transplantation of GBM-CD133$^+$ cells at doses greater than $5 \times 10^4$ cells consistently led to tumor formation in all of the recipients treated with PU-PEI only. PU-PEI-mediated miR145 delivery alone significantly reduced the tumorigenic ability of the GBM-CD133$^+$ cells in all recipients. In response to the combination of PU-PEI-mediated miR145 delivery and radiotherapy, the transplanted GBM-CD133$^+$ cells failed to form tumors at most cell doses; tumor formation was only observed at a dose of $10^5$ GBM-CD133$^+$ cells or $5 \times 10^4$ GBM-CD133$^+$ cells from certain GBM patients Importantly, the combined treatment of miR145 delivery, radiotherapy and TMZ almost eliminated tumorigenesis in all of the recipients, with the exception of one recipient of $10^5$ GBM-CD133$^+$ cells from one of the GBM patients. Gross necropsy findings and histological examinations revealed visible tumor formations with invasion in brain slices from the recipients of the GBM-CD133$^+$ cells (FIG. 7C). miR145 delivery exhibited a remarkable efficacy on tumorigenesis Importantly, the co-administration of TMZ with radiotherapy and miR145 delivery dramatically blocked tumorigenesis (FIG. 7C).

TABLE 1

Case description, tumorigenic characteristics and treatment effects of CD133+/− GBM

| | | | | Number of cells injected (cell no.) | | | | | |
|---|---|---|---|---|---|---|---|---|---|
| Case | Age/Sex | CD133$^+$ (%) | Spheres | CD133$^+$ (Vector Ctrl) | CD133$^+$ (IR) | CD133$^{++}$ (IR + TMZ) | CD133$^+$ (Mir145) | CD133$^+$ (Mir145 + IR) | CD133$^+$ (Mir145 + IR + TMZ) |
| 1 | 54/M | 3.2 | Yes | 5000 (1/3) | 5000 (0/3) | 5000 (0/3) | 5000 (0/3) | 5000 (0/3) | 5000 (0/3) |
| | | | | 10,000 (3/3) | 10,000 (3/3) | 10,000 (1/3) | 10,000 (0/3) | 10,000 (0/3) | 10,000 (0/3) |
| | | | | 50,000 (3/3) | 50,000 (3/3) | 50,000 (2/3) | 50,000 (1/3) | 50,000 (0/3) | 50,000 (0/3) |
| | | | | 100,000 (3/3) | 100,000 (3/3) | 100,000 (3/3) | 100,000 (2/3) | 100,000 (2/3) | 100,000 (0/3) |
| 2 | 68/F | 4.5 | Yes | 5000 (2/3) | 5000 (1/3) | 5000 (0/3) | 5000 (0/3) | 5000 (0/3) | 5000 (0/3) |
| | | | | 10,000 (3/3) | 10,000 (3/3) | 10,000 (0/3) | 10,000 (0/3) | 10,000 (0/3) | 10,000 (0/3) |
| | | | | 50,000 (3/3) | 50,000 (3/3) | 50,000 (2/3) | 50,000 (1/3) | 50,000 (0/3) | 50,000 (0/3) |
| | | | | 100,000 (3/3) | 100,000 (3/3) | 100,000 (3/3) | 100,000 (3/3) | 100,000 (3/3) | 100,000 (1/3) |
| 3 | 62/M | 1.2 | Yes | 5000 (2/3) | 5000 (0/3) | 5000 (0/3) | 5000 (0/3) | 5000 (0/3) | 5000 (0/3) |
| | | | | 10,000 (3/3) | 10,000 (2/3) | 10,000 (1/3) | 10,000 (0/3) | 10,000 (0/3) | 10,000 (0/3) |
| | | | | 50,000 (3/3) | 50,000 (3/3) | 50,000 (3/3) | 50,000 (1/3) | 50,000 (0/3) | 50,000 (0/3) |
| | | | | 100,000 (3/3) | 100,000 (3/3) | 100,000 (3/3) | 100,000 (1/3) | 100,000 (2/3) | 100,000 (0/3) |
| 4 | 78/M | 11.2 | Yes | 5000 (3/3) | 5000 (2/3) | 5000 (0/3) | 5000 (0/3) | 5000 (0/3) | 5000 (0/3) |
| | | | | 10,000 (3/3) | 10,000 (3/3) | 10,000 (1/3) | 10,000 (1/3) | 10,000 (0/3) | 10,000 (0/3) |
| | | | | 50,000 (3/3) | 50,000 (3/3) | 50,000 (3/3) | 50,000 (3/3) | 50,000 (2/3) | 50,000 (0/3) |
| | | | | 100,000 (3/3) | 100,000 (3/3) | 100,000 (3/3) | 100,000 (2/3) | 100,000 (3/3) | 100,000 (1/3) |

TABLE 1-continued

Case description, tumorigenic characteristics and treatment effects of CD133+/− GBM

| Case | Age/Sex | CD133+ (%) | Spheres | Number of cells injected (cell no.) | | | | | |
|---|---|---|---|---|---|---|---|---|---|
| | | | | CD133+ (Vector Ctrl) | CD133+ (IR) | CD133++ (IR + TMZ) | CD133+ (Mir145) | CD133+ (Mir145 + IR) | CD133+ (Mir145 + IR + TMZ) |
| 5 | 57/M | 4.1 | Yes | 5000 (1/3) | 5000 (0/3) | 5000 (0/3) | 5000 (0/3) | 5000 (0/3) | 5000 (0/3) |
| | | | | 10,000 (2/3) | 10,000 (0/3) | 10,000 (0/3) | 10,000 (0/3) | 10,000 (0/3) | 10,000 (0/3) |
| | | | | 50,000 (3/3) | 50,000 (3/3) | 50,000 (1/3) | 50,000 (1/3) | 50,000 (0/3) | 50,000 (0/3) |
| | | | | 100,000 (3/3) | 100,000 (3/3) | 100,000 (3/3) | 100,000 (2/3) | 100,000 (1/3) | 100,000 (0/3) |

Vector control: treated with PU-PEI empty vector only. IR only: PU-PEI empty vector combining with ionizing radiation-treated (IR: 2 Gy) only. miR145 + IR: PU-PEI-miR145 combining with IR (2 Gy). miR145 + IR + TMZ: PU-PEI-miR145 combining with IR (2 Gy) and TMZ (200 μM) treatment.

We also assessed that whether these therapeutic approaches improved the survival of the recipients of the GBM-CD133+ cells (FIG. 7D). Compared with the recipients of PU-PEI alone, radiotherapy plus TMZ administration reduced the mortality induced by GBM tumorigenesis. Interestingly, PU-PEI-mediated delivery of miR145 alone had a larger effect on survival than the combination of radiotherapy and TMZ. The additional use of radiotherapy moderately improved the survival of animals receiving PU-PEI-mediated miR145 delivery Importantly, the co-administration of TMZ with miR145 delivery and radiotherapy had the greatest effect on survival of GBM (FIG. 7D). Furthermore, quantitative RT-PCR revealed the effect of different therapeutic approaches on the expression of the oncogene Bmi-1 and various stemness factors, including Oct-4, Sox2, Nanog, Klf4, in the tumor graft (FIG. 7E). Treatment with either radiotherapy alone or the combination of radiotherapy and TMZ had only a mild inhibitory effect on the expression of these stemness factors and Bmi-1. PU-PEI-mediated delivery of miR145 alone led to a greater inhibition of expression than either radiotherapy or radiochemotherapy. Consistent with the effect on tumorigenesis (FIGS. 7A, 7B, and 7C) and recipient survival (FIG. 7D), the co-administration of TMZ with miR145 delivery and radiotherapy also effectively inhibited the gene expression of these stemness factors and Bim-1 in the tumor graft (FIG. 7E). These findings demonstrated that PU-PEI-mediated miR145 delivery is a useful approach to prevent GBM tumorigenesis in vivo, and the combination of miR145 delivery, radiotherapy, and TMZ may be a novel and effective strategy for the treatment of GBMs and GBM-CSCs.

Figure 8:
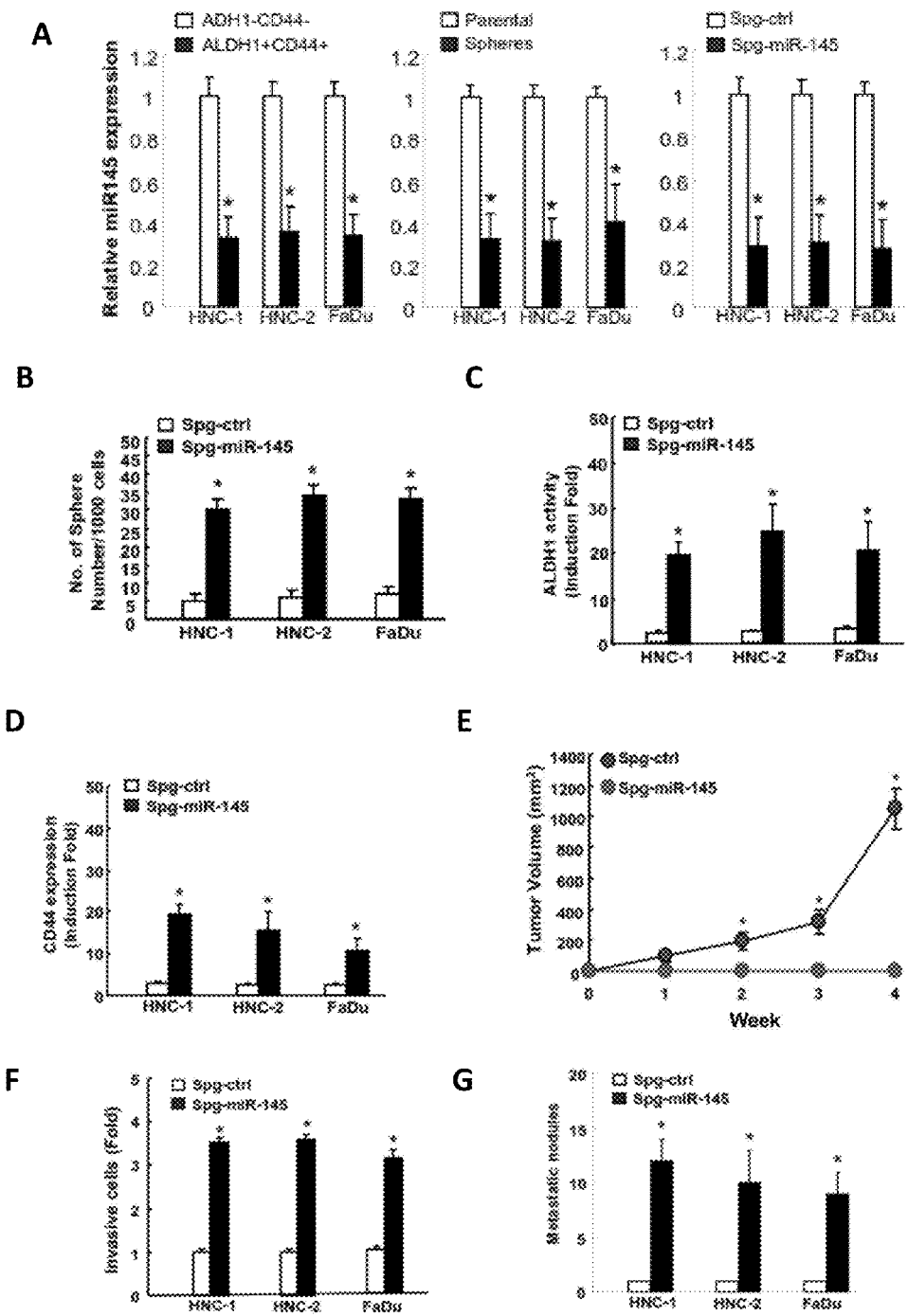
FIG. 8 shows that suppression of miR145 was crucial for ALDH$^+$/CD44$^+$/sphere-forming HNC-TICs to retain its stem-like properties; wherein FIG. 8A provides mRNA level of miR145 in ALDH$^+$/CD44$^+$ and ALDH$^-$/CD44$^-$ cells (left) as well as sphere-forming and parental cells (right) derived from 2 HNC patients specimens (HNC-1 and HNC-2) or immortalized FaDu cell line, in which the mRNA level was assessed by quantitative real-time PCR and presented as relative fold change.

8. miR145 Depletion Enhances Tumor Initiating Capability in ALDH1−CD44− non-TICs HNC The ALDH1+, CD44+, and sphere-forming HNC cells have been shown to exhibit TICs stem-like properties, and these markers have been used to identify HNC-derived tumor initiating cells (HNC-TICs). To identified the miRNA(s) involved in the regulation of TIC properties in HNC-TICs, we evaluated and compared the miRNA expression profiles in 3 pairs of HNC populations (ALDH1+ vs. ALDH1−, CD44+ vs. CD44−, and sphere-forming vs. parental) derived from patient specimens. The miRNAs that were either upregulated (>2 fold) or downregulated (<0.5 fold) in all ALDH1+, CD44+, and sphere-forming cells, in comparison to their counterparts, were considered for further analysis. The data revealed 40 miRNAs, including miR145, that were consistently upregulated or downregulated in ALDH1+, CD44+, and sphere-forming HNC cells. To further investigate whether miR145 plays a role in the identity of HNC-TICs, two patient sample-derived HNC cell lines (HNC-1 and HNC-2) and an immortalized HNC cell line (FaDu) were subjected to quantitative RT-PCR analysis to confirm that miR145 levels were low in ALDH1+/CD44+ and sphere-forming HNC cells but high in ALDH1−/CD44− and parental cells (FIG. 8A, left and middle). To evaluate the role of miR145 on cancer initiation, we knocked down miR145 in ALDH1−CD44− cells derived from HNC-1, HNC-2, and FaDu cells using an miRNA SPONGE strategy (FIG. 8A, right), and subjected these cells to functional and molecular analysis. As shown in FIGS. 8B-D, the sphere formation ability and the percentage of ALDH1+ and CD44+ cells was all elevated upon miR145 knockdown (Spg-miR145) as compared to the control (Spg-ctrl) cells. Moreover, silencing of endogenous miR145 increased the tumor repopulating ability of ALDH1−CD44− HNC cells: the growth of xenograft tumor in ALDH1−CD44−/Spg-miR145-transplanted mice was more rapid than that observed in ALDH1−CD44−/Spg-ctrl-transplanted animals (FIG. 8E); as few as 100 injected ALDH1−CD44−/Spg-miR145 cells were capable of regenerating new tumors in nude mice, whereas 100,000 ALDH1−CD44−/Spg-ctrl cells were unable to generate xenograft tumors in SCID mice. Additionally, the invasive ability of ALDH1−CD44− HNC cells was increased upon miR145 knockdown (FIG. 8F), and knockdown of miR145 also increased the number of metastatic tumor nodules in vivo (FIG. 8G). These data suggested that suppression of miR145 enables HNC cells to acquire TICs properties.

Figure 9:
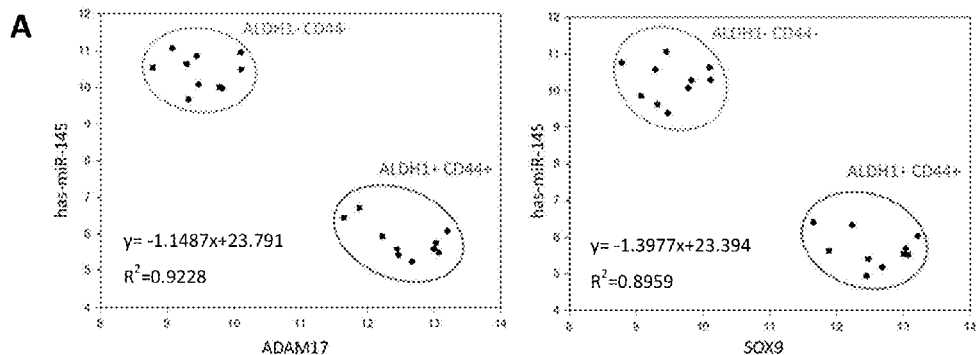
FIG. 9 shows that miR145 directly targeted to the 3'UTR of Sox9 and ADAM17; wherein FIG. 9A provides the results of the correlation analysis indicating a highly negative correlation between miR145 and Sox9 expression, as well as between miR145 and ADAM17 expression in two groups of ALDH$^+$/CD44$^+$ and ALDH$^-$/CD44$^-$ cells derived from HNC patient samples.
Figure 9:
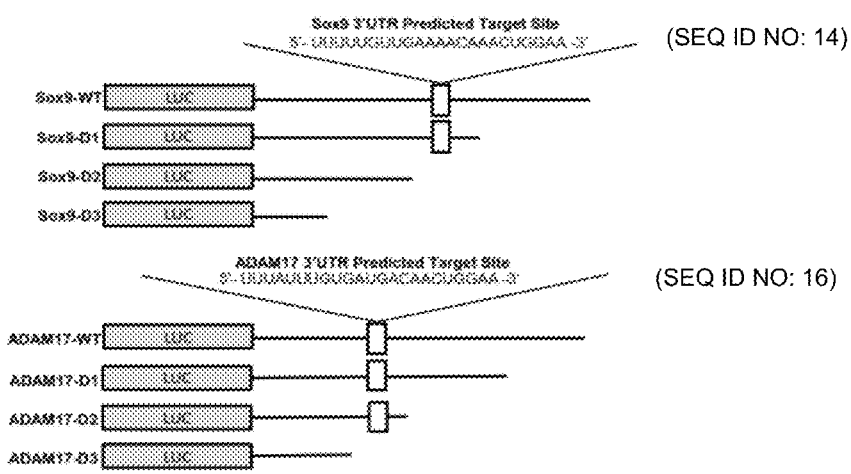

9. miR145 Directly Targets the 3'UTR of SOX9 and ADAM17 and Suppresses the Tumor-Initiating Properties of HNC Cells To identify the downstream targets of miR145 with respect to the regulation of stem-like properties of HNC-TICs, 3 pairwise comparisons of HNC cell populations were subjected to a cDNA microarray analysis focusing on stemness-related genes, and the results were further subjected to a prediction algorithm of miR145 targets. Our results identified SOX9 and ADAM17 as potential targets of miR145 that were highly expressed in ALDH1+CD44+, sphere-forming, and Spg-miR145 HNC cells in relation to ALDH1−CD44−, parental, and Spg-ctrl HNC cells, respectively. Analysis of the expression levels of miR145, SOX9, and ADAM17 in cell subpopulations from patient specimens (ALDH1+CD44+ and ALDH1−CD44−) revealed an inverse correlation between miR145 and SOX9/ADAM17 (FIG. 9A). Using the Target Scan program, we found predicted potential miR145 targeting sites within the 3'UTR of SOX9 and ADAM17 3'UTR (FIG. 9B). We then constructed a series of reporter plasmids containing either wild type (WT), mutated (Mut), or deleted forms (D1-D3) of the SOX9 and ADAM17 3'UTR. We performed reporter assays in HNC-1 and HNC-2 cells and found that lentiviral-mediated miR145 delivery suppressed the luciferase activities of the reporters containing predicted miR145 targeting sites (50X9-WT, SOX9-D1, ADAM17-WT, ADAM17-D1, and ADAM17-D2), but not the reporters with deleted targeting sites (FIG. 9C, top). Mutations within the miR145 targeting sites also hindered the inhibitory effect of miR145 on the reporter constructs (FIG. 9C, bottom). These data demonstrated that miR145 directly targets SOX9 and ADAM17 through their 3'UTR regions. In line with these data, overexpression of miR145 in ALDH1$^+$CD44$^+$ HNC cells by lentivirus-mediated transfection (FIG. 9D) decreased the protein levels of SOX9 and ADAM17, whereas Spg-miR145 treatment of ALDH1$^-$CD44$^-$ cells increased SOX9 and ADAM17 protein expression (FIG. 9E). Remarkably, co-knockdown of SOX9/ADAM17 in ALDH1$^+$CD44$^+$ cells using SOX9- and ADAM17-specific shRNAs (FIG. 9F) had similar effects as miR145 overexpression, resulting in a reduction in sphere-forming ability, reduced percentages of CD44$^+$ and ALDH1$^+$ cells, and reduced invasive capacity (data not shown). Animal study showed that overexpression of miR145, as well as the knockdown of SOX9 and ADAM17, effectively inhibited tumor-initiating property in ALDH1$^+$CD44$^+$ cells-transplanted grafts in NOD-SCID mice (FIG. 9G). Our results suggest that miR145 directly targets the 3'UTR of SOX9 and ADAM17 to suppress their expression and repress the TIC properties of ALDH1$^+$CD44$^+$ HNC cells.

Figure 10:
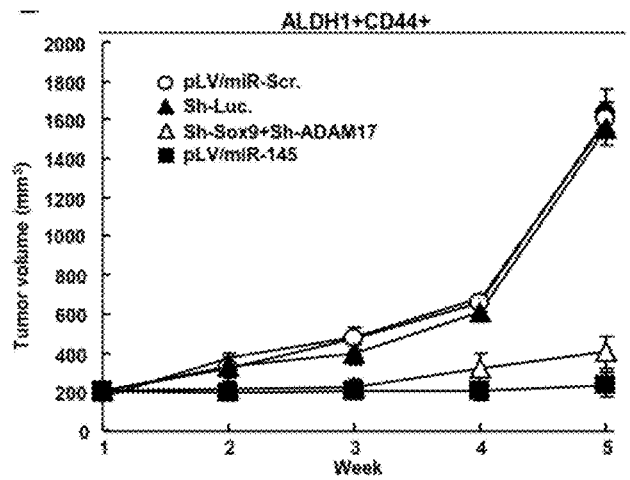
FIG. 10 shows that delivery of miR145 in HNC-TICs-transplanted mice attenuated tumor progression in vivo; wherein FIGS. 10A and 10B provide the effects of miR145 on the tumor size and overall survival in mice, respectively.
Figure 10:
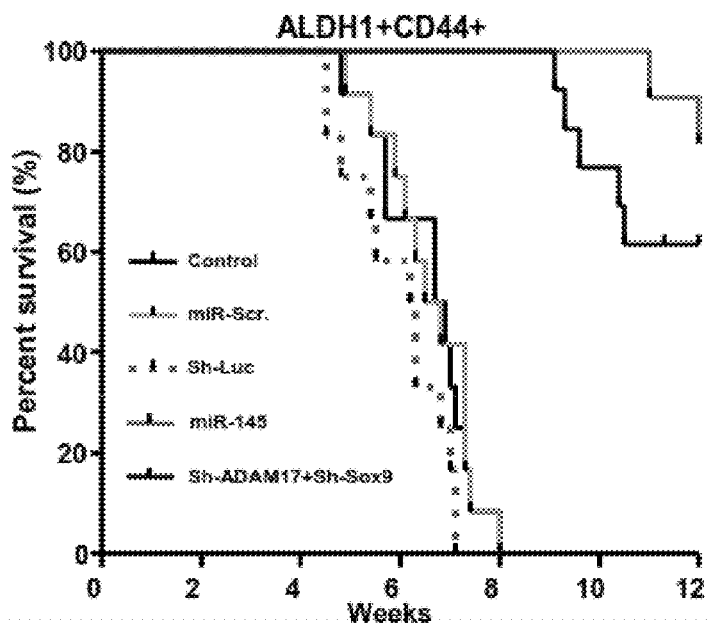

10. Therapeutic Delivery of miR145 in HNC-ALDH1$^+$CD44$^+$-transplanted Mice Attenuates Tumor Progression in vivo We further explored the therapeutic potential of miR145 in immunocompromised mice bearing HNC-TIC xenografted tumors. Nude mice that were orthotopically pre-injected with GFP-labeled ALDH1$^+$CD44$^+$ cells in the neck region were treated with miR145-overexpressing lentivirus (pLV-miR-145) and shSOX9+shADAM17 by intra-tumoral lesion injection. As shown in FIG. 10A, five weeks after treatment, pLV-miR145 and shSOX9+shADAM17 dramatically reduced tumor size in comparison to mice that received empty vector (pLV) or shRNA control (shLuc). By monitoring the treated mice for up to 12 weeks, we observed that administration of pLV-miR145 or shSOX9+shADAM17 prolonged animal survival to a greater extent than did the LNA-miR145 treatment (FIG. 10B). Collectively, our data demonstrate that miR145 treatment impaired tumor growth, reduced miR145 downstream target expression, suppressed metastasis, and improved the survival of HNC tumor-bearing mice.

Figure 11:
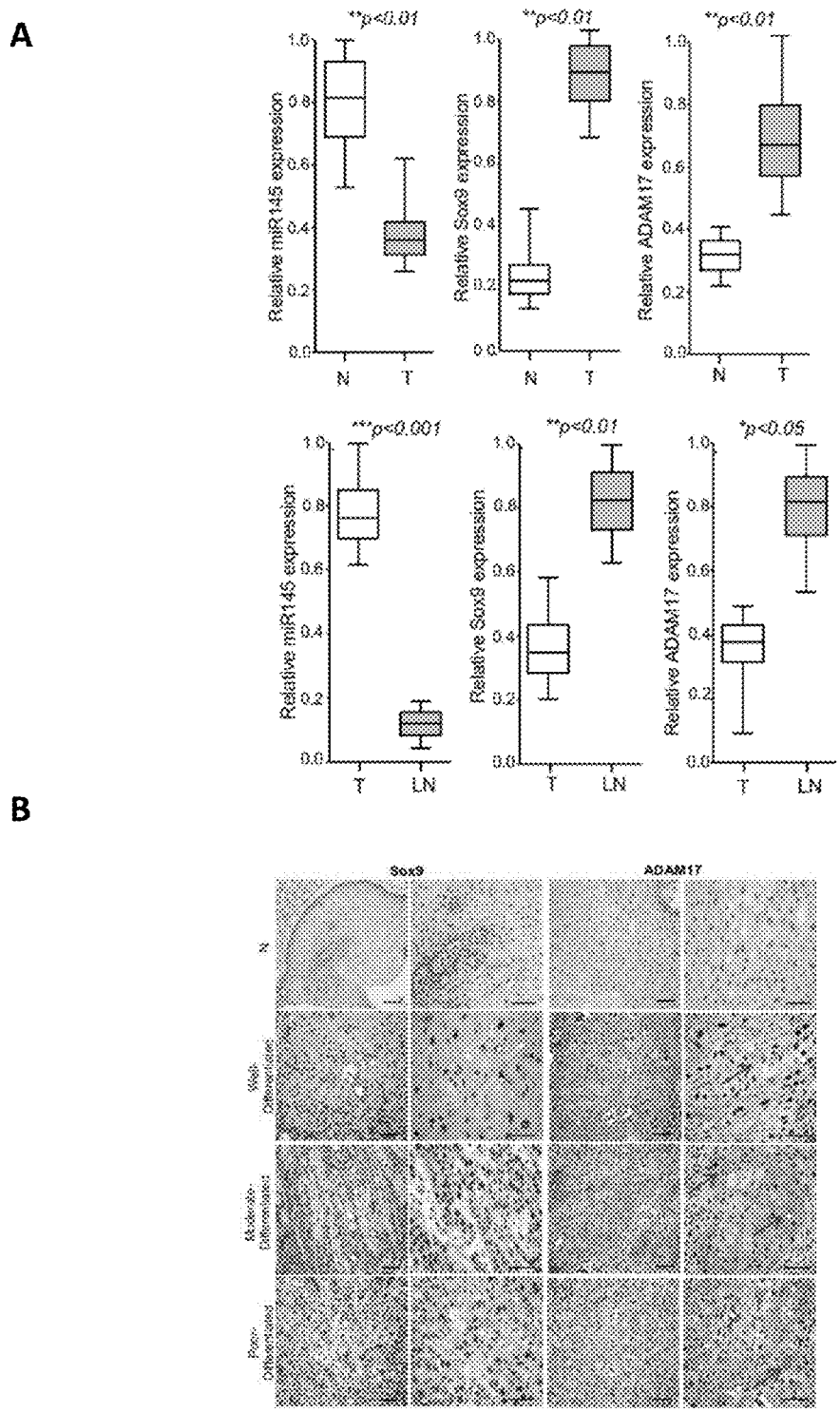
FIG. 11 shows that the miR145$^{low}$Sox9$^{high}$ADAM17$^{high}$ signature predicts poor survival in HNC patients; wherein FIG. 11A provides the results of histological analysis for the expression levels of miR145, SOX9, and ADAM17 in paired tissue samples from tumor (T; n=75) and adjacent non-tumor parts (N; n=75), as well as from lymph node metastatic (LN; n=50) and local (T; n=50) lesions in HNC patient tissues.

11. Clinical Significance of the miR145$^{low}$SOX9$^{high}$ADAM17$^{high}$ Signature in HNC Patients To validate the significance of the miR145-SOX9/ADAM17 axis in clinical specimens, we collected paired samples of tumor (T) and non-tumor (N) tissue from HNC patients and subjected these samples to histological analysis. The expression of miR145 in HNC tissues was significantly decreased in the tumor specimens, while SOX9 and ADAM17 expression was increased relative to the non-tumor tissue (FIG. 11A, top). We also compared the levels of these molecules between lymph node metastatic (LN) and local (T) lesions in HNC patient tissues. In line with our previous data, the level of miR145 expression was higher in local tumor samples but lower in metastatic lesions, whereas SOX9/ADAM17 expression levels were lower in local tumor samples and higher in metastatic lesions (FIG. 11A, bottom). We further compared the expression of SOX9 and ADAM17 in a panel of HNC patient samples from non-tumor and poorly differentiated tumor specimens. IHC staining demonstrated that high-grade with poor differentiated HNC tumor tissues had high levels of SOX9 and ADAM17 expression while low-grade tumor samples presented with low levels of SOX9 and ADAM17 (FIG. 7B). To determine the prognostic significance of miR145, SOX9, and ADAM17 expression levels, a Kaplan-Meier survival analysis of HNC patients was performed according to the expression profiles of these genes. This survival analysis of HNC patients showed that patients with tumors that expressed high levels of SOX9 and ADAM17 had a reduced survival rate, whereas patients with high tumoral expression of miR145 had a better survival rate. Moreover, patients with tumors that displayed an expression profile of miR145$^{low}$SOX9$^{high}$ADAM17$^{high}$ had a lower survival rate as compared to patients harboring tumors with other profiles, such as miR145$^{high}$SOX9$^{low}$ADAM17$^{low}$ (FIG. 11C). Overall, these results suggest that suppressed expression of miR145 and elevated expression of SOX9/ADAM17 are strongly associated with advanced-grade HNC and a worse prognosis. Thus, the miR145$^{low}$SOX9$^{high}$ADAM17$^{high}$ signature could be used as a predictor for disease progression and clinical outcome in HNC patients.

We claim:

1. A method for inhibiting cancer stem cell-like and chemoradioresistant properties of glioblastoma multiforme associated cancer stem cells (GBM-CSCs) or head and neck cancer-derived tumor initiating cells (HNC-TICs) comprising delivering miR145 to the GBM-CSCs or HNC-TICs in an amount effective in inhibiting cancer stem cell-like and chemoradioresistant properties of said cells.

2. The method of claim 1, wherein the miR145 is encapsulated in a polymer as a delivery vehicle.

3. The method of claim 2, the polymer is a polyurethane (PU).

4. The method of claim 3, the polyurethane is a synthesized polyurethane (PU) with short branch polyetherimide (sbPEI).

5. The method of claim 1, wherein the GBM-CSCs are GBM-CD133$^+$ cells and GBM-SF$^+$ cells.

6. The method of claim 1, wherein the HNC-TICs are ALDH1$^+$, CD44$^+$, and sphere-forming HNC cells.

7. A method for treating a brain tumor associated with GBM-CSCs comprising administering to a subject in need thereof miR145in an amount effective in inhibiting cancer stem cell-like and chemoradioresistant properties of the GBM-CSCs through a delivery vehicle.

8. The method of claim 7, the delivery vehicle is a PU.

9. The method of claim 8, the PU is a synthesized PU-sbPEI.

10. The method of claim 7, which further comprises treating the subject with radiotherapy or an anti-cancer drug.

11. The method of claim 10, wherein the anti-cancer drug is temozolomide.

12. The method of claim 7, wherein the GBM-CSCs are GBM-CD133$^+$ cells and GBM-SF$^+$ cells.

13. A method for treating a HNC associated with HNC-TICs comprising administering to a subject in need thereof miR145in an amount effective in inhibiting cancer stem cell-like and chemoradioresistant properties of the HNC-TICs through a delivery vehicle.

14. The method of claim 13, wherein the miR145 is carried by a vector.

15. The method of claim 14, wherein the vector is selected from the group consisting of a plasmid, cosmid, phagemid or a virus.

16. The method of claim 13, wherein the HNC-TICs are ALDH1$^+$, CD44$^+$, and sphere-forming HNC cells.

* * * * *

SEQUENCE LISTING

```
<160> NUMBER OF SEQ ID NOS: 29

<210> SEQ ID NO 1
<211> LENGTH: 25
<212> TYPE: DNA
<213> ORGANISM: Artificial Sequence
<220> FEATURE:
<223> OTHER INFORMATION: Oct4 3'UTR forward

<400> SEQUENCE: 1
ggtgcctgcc cttctaggaa tgggg                                         25

<210> SEQ ID NO 2
<211> LENGTH: 27
<212> TYPE: DNA
<213> ORGANISM: Artificial Sequence
<220> FEATURE:
<223> OTHER INFORMATION: Oct4 3'UTR reverse

<400> SEQUENCE: 2
aagtgtgtct atctactgtg tcccagg                                       27
```

<210> SEQ ID NO 3
<211> LENGTH: 25
<212> TYPE: DNA
<213> ORGANISM: Artificial Sequence
<220> FEATURE:
<223> OTHER INFORMATION: Sox2 3'UTR forward

<400> SEQUENCE: 3
gggccggaca gcgaactgga ggggg                                      25

<210> SEQ ID NO 4
<211> LENGTH: 28
<212> TYPE: DNA
<213> ORGANISM: Artificial Sequence
<220> FEATURE:
<223> OTHER INFORMATION: Sox2 3'UTR reverse

<400> SEQUENCE: 4
cagtgtccat atttcaaaaa tttattta                                   28

<210> SEQ ID NO 5
<211> LENGTH: 35
<212> TYPE: DNA
<213> ORGANISM: Artificial Sequence
<220> FEATURE:
<223> OTHER INFORMATION: Sox9 3'UTR forward

<400> SEQUENCE: 5
atgcactagt ggaggcctcc cacgaagggc gaaga                           35

<210> SEQ ID NO 6
<211> LENGTH: 37
<212> TYPE: DNA
<213> ORGANISM: Artificial Sequence
<220> FEATURE:
<223> OTHER INFORMATION: Sox9 3'UTR reverse

<400> SEQUENCE: 6
atgcgtttaa accttttttaa tgcaatgtat atttatt                        37

<210> SEQ ID NO 7
<211> LENGTH: 35
<212> TYPE: DNA
<213> ORGANISM: Artificial Sequence
<220> FEATURE:
<223> OTHER INFORMATION: ADAM17 3'UTR forward

<400> SEQUENCE: 7
atgcactagt tttagttctc agctcttctg actta                           35

<210> SEQ ID NO 8
<211> LENGTH: 35
<212> TYPE: DNA
<213> ORGANISM: Artificial Sequence
<220> FEATURE:
<223> OTHER INFORMATION: ADAM17 3'UTR reverse

<400> SEQUENCE: 8
atgcaagctt gaggcagagt ctcactctgt caccc                           35

<210> SEQ ID NO 9
<211> LENGTH: 23
<212> TYPE: RNA
<213> ORGANISM: Artificial Sequence
<220> FEATURE:
<223> OTHER INFORMATION: miR145

-continued

<400> SEQUENCE: 9
guccaguuuu cccaggaauc ccu                                    23

<210> SEQ ID NO 10
<211> LENGTH: 23
<212> TYPE: RNA
<213> ORGANISM: Artificial Sequence
<220> FEATURE:
<223> OTHER INFORMATION: Oct4 3'UTR

<400> SEQUENCE: 10
aggggaguuu ggggcaacug guu                                    23

<210> SEQ ID NO 11
<211> LENGTH: 23
<212> TYPE: RNA
<213> ORGANISM: Artificial Sequence
<220> FEATURE:
<223> OTHER INFORMATION: mutOct4 3'UTR

<400> SEQUENCE: 11
auuggaguuu ugugcaauuc uuu                                    23

<210> SEQ ID NO 12
<211> LENGTH: 20
<212> TYPE: RNA
<213> ORGANISM: Artificial Sequence
<220> FEATURE:
<223> OTHER INFORMATION: Sox2 3'UTR

<400> SEQUENCE: 12
ggccggacag cgaacuggag                                        20

<210> SEQ ID NO 13
<211> LENGTH: 20
<212> TYPE: RNA
<213> ORGANISM: Artificial Sequence
<220> FEATURE:
<223> OTHER INFORMATION: mutSox2 3'UTR

<400> SEQUENCE: 13
ggcggaacag cgcgcuaaag                                        20

<210> SEQ ID NO 14
<211> LENGTH: 23
<212> TYPE: RNA
<213> ORGANISM: Artificial Sequence
<220> FEATURE:
<223> OTHER INFORMATION: Sox9 3'UTR

<400> SEQUENCE: 14
uuuuuguuga aaacaaacug gaa                                    23

<210> SEQ ID NO 15
<211> LENGTH: 23
<212> TYPE: RNA
<213> ORGANISM: Artificial Sequence
<220> FEATURE:
<223> OTHER INFORMATION: mutSox9 3'UTR

<400> SEQUENCE: 15
uuuuuguuga aaacacagua gca                                    23

<210> SEQ ID NO 16
<211> LENGTH: 23

```
<212> TYPE: RNA
<213> ORGANISM: Artificial Sequence
<220> FEATURE:
<223> OTHER INFORMATION: ADAM17 3'UTR

<400> SEQUENCE: 16
uuuauuugug augacaacug gaa                                           23

<210> SEQ ID NO 17
<211> LENGTH: 23
<212> TYPE: RNA
<213> ORGANISM: Artificial Sequence
<220> FEATURE:
<223> OTHER INFORMATION: mutADAM17 3'UTR

<400> SEQUENCE: 17
uuuauuugug augacagauc gca                                           23

<210> SEQ ID NO 18
<211> LENGTH: 37
<212> TYPE: DNA
<213> ORGANISM: Artificial Sequence
<220> FEATURE:
<223> OTHER INFORMATION: Sox9-D1

<400> SEQUENCE: 18
atgcgtttaa acccacacac acacacaata taaggca                            37

<210> SEQ ID NO 19
<211> LENGTH: 37
<212> TYPE: DNA
<213> ORGANISM: Artificial Sequence
<220> FEATURE:
<223> OTHER INFORMATION: Sox9-D2

<400> SEQUENCE: 19
atgcgtttaa accggggggca gtgtgctcgg gcactta                           37

<210> SEQ ID NO 20
<211> LENGTH: 37
<212> TYPE: DNA
<213> ORGANISM: Artificial Sequence
<220> FEATURE:
<223> OTHER INFORMATION: Sox9-D3

<400> SEQUENCE: 20
atgcgtttaa actttatcta aaaatatgta taaatcc                            37

<210> SEQ ID NO 21
<211> LENGTH: 35
<212> TYPE: DNA
<213> ORGANISM: Artificial Sequence
<220> FEATURE:
<223> OTHER INFORMATION: ADAM17-D1

<400> SEQUENCE: 21
atgcaagctt aattcaactg gctaccatgt atagc                              35

<210> SEQ ID NO 22
<211> LENGTH: 36
<212> TYPE: DNA
<213> ORGANISM: Artificial Sequence
<220> FEATURE:
<223> OTHER INFORMATION: ADAM17-D2

<400> SEQUENCE: 22
```

```
atgcaagctt caaaaaaaaa aaaaaaaaaa aaaaac                                36
```

<210> SEQ ID NO 23
<211> LENGTH: 35
<212> TYPE: DNA
<213> ORGANISM: Artificial Sequence
<220> FEATURE:
<223> OTHER INFORMATION: ADAM17-D3

<400> SEQUENCE: 23

```
atgcaagctt aaaacctgaa agcctcaaaa taagc                                 35
```

<210> SEQ ID NO 24
<211> LENGTH: 41
<212> TYPE: DNA
<213> ORGANISM: Artificial Sequence
<220> FEATURE:
<223> OTHER INFORMATION: sponge forward

<400> SEQUENCE: 24

```
gatccaggga ttcctcccaa actggacaga tctggccgca c                          41
```

<210> SEQ ID NO 25
<211> LENGTH: 41
<212> TYPE: DNA
<213> ORGANISM: Artificial Sequence
<220> FEATURE:
<223> OTHER INFORMATION: sponge reverse

<400> SEQUENCE: 25

```
tcgagtgcgg ccagatctgt ccagtttggg aggaatccct g                          41
```

<210> SEQ ID NO 26
<211> LENGTH: 42
<212> TYPE: DNA
<213> ORGANISM: Artificial Sequence
<220> FEATURE:
<223> OTHER INFORMATION: scramble forward

<400> SEQUENCE: 26

```
gatcccatta atgtcggaca actcaatcag atctggccgc ac                         42
```

<210> SEQ ID NO 27
<211> LENGTH: 44
<212> TYPE: DNA
<213> ORGANISM: Artificial Sequence
<220> FEATURE:
<223> OTHER INFORMATION: scramble reverse

<400> SEQUENCE: 27

```
tcgagtgcgg ccagatctga ttgagttgtc cgacacatta atgg                       44
```

<210> SEQ ID NO 28
<211> LENGTH: 21
<212> TYPE: DNA
<213> ORGANISM: Artificial Sequence
<220> FEATURE:
<223> OTHER INFORMATION: target sequence for Sox9-knockdown (Sh-RNA)

<400> SEQUENCE: 28

```
gcggaggaag tcggtgaaga a                                                21
```

<210> SEQ ID NO 29
<211> LENGTH: 21
<212> TYPE: DNA
<213> ORGANISM: Artificial Sequence

```
<220> FEATURE:
<223> OTHER INFORMATION: target sequence for ADAM17-knockdown (Sh-RNA)

<400> SEQUENCE: 29
cctatgtcga tgctgaacaa a                                              21
```